US005858376A

United States Patent [19]
Johnson et al.

[11] Patent Number: 5,858,376
[45] Date of Patent: Jan. 12, 1999

[54] HSV PROTEINS FOR INHIBITING RECOGNITION BY CYTOTOXIC T LYMPHOCYTES

[75] Inventors: David C. Johnson, 107 Traymore, Hamilton, Ontario, Canada, L8S 1R8; Ian A. York, Apt. 1207 644 Main Street, Hamilton, Ontario, Canada, L8S 1A1

[73] Assignees: David C. Johnson, Portland, Oreg.; Ian A. York, Worcester, Mass.

[21] Appl. No.: 476,412

[22] Filed: Jun. 7, 1995

Related U.S. Application Data

[62] Division of Ser. No. 159,890, Nov. 30, 1993.
[51] Int. Cl.$^6$ .................... A61K 39/245; A01N 43/08; C12N 15/38; C07K 14/005
[52] U.S. Cl. .................. 424/229.1; 514/44; 435/172.3; 435/320.1; 435/240.2; 530/350; 536/23.5; 536/23.72
[58] Field of Search .................... 514/44; 435/172.3, 435/320.1, 240.2; 536/23.5, 23.72; 530/350; 424/229.1

[56] References Cited

PUBLICATIONS

Koelle et al. J Clin Invest vol. 91, Mar. 1993, pp. 961–968.
Coghlan. New Scientist, 25 Nov. 1995, pp. 14–15.
Posavad et al. J Virol, vol. 66, No. 11, Nov. 1992, pp. 6264–6272.
Palfreyman, et al., "Successful Use of Oligopeptides as Immunogens in the Preparation of Antisera to Immediate–Early Gene Products of Herpes Simplex Virus Type 1," *The Journal of General Virology*, The Society for General Microbiology, vol. 65, Part 5, pp. 865–874 (1984).
Persson, et al., "Cells that Constitutively Express the Herpes Simplex Virus Immediate–Early Protent ICP4 Allow Efficient Activation of Viral Delayed–Early Genes in *trans*," *The Journal of General Virology*, American Society for Microbiology, vol. 54, No. 2, pp. 414–421 (1985).
McGeoch, et al., "Sequence Determination and Genetic Content of the Short Unique Region in the Genome of Herpes Simplex Virus Type 1," *Journal of Molecular Biology*, Academic Press Inc. (London) Ltd., vol. 181, pp. 1–13 (1985).
Carter, et al., "Mapping of a Herpes Simplex Virus Type 2–Encoded Function That Affects the Susceptability of Herpes Simplex Virus–Infected Target Cells to Lysis by Herpes Simplex Virus–Specific Cytotoxic T Lymphocytes," *Journal of Virology*, American Society for Microbiology, vol. 49, No. 3, pp. 766–771 (1984).
Fletcher III, et al., "DNA Sequence and Genetic Organization of the Unique Short ($U_s$) Region of the Simian Varicella Virus Genome," *Virology* Academic Press, Inc., vol. 193, pp. 762–773 (1993).
McGeoch, et al., "The Complete DNA Sequence of the Long Unique Region in the Genome of Herpes Simplex Virus Type 1," *Journal of General Virology*, SGM, vol. 69, pp. 1531–1547 (1988).

McGeoch, et al., "Herpes Simplex Virus" (1992).
Mavromara–Nazos, et al., "Construction and Properties of a Viable Herpes Simplex Virus 1 Recombinant Lacking Coding Sequences of the α47 Gene," *Journal of Virology*, American Society for Microbiology, vol. 60, No. 2 pp. 807–812 (1986).
Nishiyama, et al., "The US 9, 10, 11, and 12 Genes of Herpes Simplex Virus Type 1 Are of No Importance for Its Neurovirulence and Latency in Mice," *Virology*, Academic Press, Inc., vol. 194, pp. 419–423 (1993).
Whitley, "Herpes Simplex Viruses," *Virology*, Raven Press, Ltd., Chapter 66, pp. 1843–1887 (1990).
Marsden, et al., "Genomic Location and Lack of Phosphorylation of the HSV Immediate–Early Polypeptide IE 12," *Journal of General Virology*, SGM, vol. 62, pp. 17–27 (1982).
Davidson, et al., "Evolutionary Comparisons of the S Segments in the Genomes of Herpes Simplex Virus Type 1 and Varicella–Zoster Virus," *Journal of General Virology*, SGM, vol. 67, pp. 597–611 (1986).
Zhang, et al., "The structure of the pseudorabies virus genome at the end of the inverted repeat sequences proximal to the junction with the short unique region," *Journal of General Virology*, SGM, vol. 71, pp. 2433–2441 (1990).
Umene, "Conversion of a Fraction of the Unique Sequence to Part of the Inverted Repeats in the S Component of the Herpes Simplex Virus Type 1 Genome," *Journal of General Virology*, SGM, vol. 67, pp. 1035–1048 (1986).
Johnson, et al., "Intracellular Transport of Herpes Simplex Virus gD Occurs More Rapidly in Uninfected Cells that in Infected Cells," *Journal of Virology*, American Society for Microbiology, vol. 54, No. 3, pp. 682–689 (1985).
del Val, et al., "Cytomegalovirus Prevents Antigen Presentation by Blocking the Transport of Peptide–loaded Major Histocompatibility Complex Class I Molecules into the Medial–Golgi Compartment," *J. Exp. Med.* The Rockefeller University Press, vol. 176, pp. 729–738 (1992).
Gooding, "Virus Proteins That Counteract Host Immune Defenses," *Minireview*, Cell Press, vol. 71, pp. 5–7 (1992).
Mellencamp et al., "Pseudorabies Virus–Induced Suppression of Major Histovompatibility Complex Class I Antigen Expression," *Journal of Virology*, American Society of Microbiology, vol. 65, No. 6, pp. 3365–3368 (1991).

*Primary Examiner*—Ponnathapura Achutamurthy
*Assistant Examiner*—Phuong T. Bui
*Attorney, Agent, or Firm*—Kenyon & Kenyon

[57] ABSTRACT

This invention relates to the use of Herpes Simplex Virus (HSV) immediate early proteins ICP47 or IE12, nucleic acid sequences coding for ICP47 and IE12, and homologous proteins and nucleic acid sequences, to inhibit presentation of viral and cellular antigens associated with major histocompatibility class I (MHC class I) proteins to CD8+T lymphocytes. This inhibition effectively increases infective persistence, which can improve the utility of viral gene therapy vectors. This invention also relates to a method of inhibiting recognition of a cell by cytotoxic T lymphocytes, comprising introducing into the cell an isolated protein of ICP47 of HSV type 1 or IE12 of HSV type 2. In addition, this invention pertains to vector elements, vectors, polypeptides and polypeptide fragments that can be utilized for these purposes.

2 Claims, 8 Drawing Sheets

HSV PROTEINS FOR INHIBITING RECOGNITION BY CYTOTOXIC T LYMPHOCYTES

This application is a division of application Ser. No. 08/159,890, filed on Nov. 30, 1993.

SUMMARY OF THE INVENTION

This invention relates generally to the use of isolated viral proteins and isolated viral nucleic acids to inhibit the ability of the immune system to recognize and then destroy virus-infected cells or other cells. This invention also relates generally to the inhibition of viral genes, mRNA and proteins in vivo in order to increase immune recognition of infected cells and other cells. More specifically, the invention relates to the use of Herpes Simplex Virus (HSV) immediate early protein ICP47, DNA sequences coding for ICP47, and homologous proteins and DNA sequences, to inhibit presentation of viral and cellular antigens associated with major histocompatibility class I (MHC class I) proteins to T lymphocytes. This inhibition effectively increases infective persistence, which can, for example, improve the utility of viral gene therapy vectors. This invention also more specifically pertains to methods for inhibiting expression and/or activity of the ICP47 protein, which can increase immune recognition of herpesvirus-infected cells and other cells, and which can, for example, serve as a means of treating herpesvirus infections.

BACKGROUND OF THE INVENTION

The normal mammalian immune system responds to viral infection in a variety of ways. One important response is that T lymphocytes become able to recognize and kill virus-infected cells, while leaving non-infected cells unharmed. Since viruses multiply by taking over the cell's machinery, when T lymphocytes kill the virus-infected cell they thereby limit the ability of the virus to reproduce itself.

The ability of T lymphocytes to kill only infected cells is mediated by the ability of the infected cells to produce certain "signals". These "signals" which are protein-peptide complexes called major histocompatibility (MHC) complexes, are produced by mammalian cells in response to viral infection. These complexes are then transported to the surface of the infected cells, where they are "displayed" to other cells, most notably T lymphocytes. As T lymphocytes circulate in the body, they come into contact with cells that have MHC complexes on their surfaces. If those MHC complexes have associated with them viral or foreign antigens in the form of small fragments of viral or foreign proteins, receptors on the surfaces of the T lymphocytes become activated, and the T lymphocytes are induced to kill those cells. But when T lymphocytes come into contact with cells that do not have the viral or foreign antigens associated with the MHC complexes on their surface, the T lymphocytes do not disturb them. (Yewdell, J. W., and Bennink, J. R., *Cell biology of antigen processing and presentation to major histocompatibility complex class I molecule-restricted T lymphocytes*, Adv. Immunol. 52:1–123 (1992)).

There are two classes of MHC complexes, class I and class II. The production and display of MHC class I complexes is fairly well understood. Infected cells are able to degrade viral proteins to some extent, and short protein pieces, or peptides, are produced as a result. These peptides are transported from the nucleus or cytoplasm to the endoplasmic reticulum (ER) or to the Golgi apparatus; the ER and Golgi apparatus are convoluted, membranous intracellular organs involved in the post-translational processing of proteins, and in their transport to the cell surface. Once inside the ER or Golgi apparatus, the peptides bind to the MHC class I protein α-chains and β-2-microglobulin, to form a trimolecular complex (Townsend, A., Öhlén, C., Bastin, J., Ljunggren, H. G., Foster, L., and Kärre, K. *Association of class I major histocompatibility heavy and light chains induced by viral peptides*, Nature 340:443–448 (1989)). This complex is then transported to the cell surface, where it can be recognized by T lymphocyte receptors. Receptors on the surface of a particular type of T lymphocytes, known as virus-specific CD8+ T lymphocytes, specifically recognize the MHC class I complexes that are formed by the combination of MHC class I proteins and peptides derived from a particular virus, and induce the CD8+ lymphocytes to kill the cells that bear those complexes.

The presentation of MHC class I complexes and their recognition by CD8+ T lymphocytes has been also implicated in a variety of human and animal afflictions other than viral infection. Perhaps the first role identified for MHC class I complexes was their role in tissue transplant rejection, which is why they are called "Major Histocompatibility Complexes" (MHC). MHC Class I complexes appear to be of particular importance in skin graft rejection. (Zijlstra, M., Auchincloss, H., Loring, J., Chase, C., Russell, P., and Jaenisch, R., *Skin graft rejection by $β^2$-microglobulin-deficient mice*, J. Exp. Med. 175:885–893 (1992)). In addition, a large number of autoimmune diseases are believed to be the result of CD8+ T lymphocytes attacking cells displaying MHC class I complexes. For example, there is evidence that attack by CD8+ T lymphocytes plays a role in multiple sclerosis (see Steinman, L., *Autoimmune disease* Sci. Amer. 269(3):106–114), diabetes (Oldstone, M. B. A., Nerenberg, M., Southern, P., Price, J., and Lewicki, H., *Virus infection triggers insulin-dependent diabetes mellitus in a transgenic model: role of anti-self (virus) immune response*, Cell 65:319–331 (1991)), and arthritis (Braun, W. E., *HIA molecules in autoimmune diseases*, Clin. Biochem. 25(3):187–191 (1992); Scarpa, R., Del Puente, A., di Girolamo, C., della Valle, G., Lubrano, E., and Oriente, P., *Interplay between environmental factors, articular involvement, and HLA-B7 in patients with psoriatic arthritis*, Annals of Rheumatic Dis. 51:78–79 (1992)).

Although viral infection usually results in the display and recognition of MHC complexes, there are a number of animal viruses that are able to persist in the body, despite these mechanisms in the immune system that usually detect and destroy infected cells. Some such persistent viruses produce an extended or even constant infection, while others are able to become dormant or latent for long periods and then reappear to reinfect the individual. It is now recognized that some of these viruses evade detection by producing proteins that interfere with or block the cell's ability to make or display MHC class I complexes (Gooding, L. R., *Virus proteins that counteract host defenses*, Cell 71:5–7 (1992)).

Different persistent viruses appear to interfere with different stages in the production and display of MHC complexes. For example, the Ela gene of adenovirus type 12 produces a protein that blocks transcription of the MHC class I genes, thus preventing the production of the MHC class I proteins themselves (Schrier, P. I., Bernards, R., Vaessen, R. T. M. J., Houweling, A., and van der Eb, A. J., *Expression of class I major histocompatability antigens switched off by highly oncogenic adenovirus 12 in transformed rat cells*, Nature 305:771–775 (1983)). The E3 gene of human adenovirus types 2 and 5 produces a 19 thousand dalton (KD) protein that binds to the MHC class I proteins and causes them to remain sequestered or "stuck" in the ER or Golgi apparatus (Burgert, H.-G., and Kvist, S., *An adenovirus type 2 glycoprotein blocks cell surface expression of human histocomoatibility class I antigens*, Cell 41:987–997 (1985)). Similarly, murine cytomegalovirus produces a protein that inhibits the transport of the completed protein-peptide complexes from the Golgi apparatus to the cell surface (del Val, M., Hengel, H., Häcker, H., Hartlaub, U., Ruppert, T., Lucin, P., and Koszinowski, U. H., *Cytomegalovirus prevents antigen presentation by blocking the transport of peptide-loaded major histocomoatibility complex class I molecules into the media-golgi compartment*, J. Exp. Med. 176:729–738 (1992)). Using an apparently very different mechanism, myxoma virus appears to cause the MHC class I proteins to be removed from the cell surface (Boshkov, L. K., Macen, J. L., and McFadden, G., *Virus-induced loss of class I MHC antigens from the surface of cells infected with myxoma virus and malignant rabbit fibroma virus*, J. Immunol. 148:881–887 (1992)).

Herpes simplex virus (HSV) types 1 and 2 are persistent viruses that commonly infect humans; they cause a variety of troubling human diseases. HSV type 1 causes oral "fever blisters" (recurrent herpes labialis), and HSV type 2 causes genital herpes, which has become a major venereal disease in many parts of the world. No fully satisfactory treatment for genital herpes currently exists. In addition, although it is uncommon, HSV can also cause encephalitis, a life-threatening infection of the brain. (*The Merck Manual*, Holvey, Ed., 1972; Whitley, *Herpes Simplex Viruses*, In: Virology, 2nd Ed., Raven Press (1990)).

A most serious HSV-caused disorder is dendritic keratitis, an eye infection that produces a branched lesion of the cornea, which can in turn lead to permanent scarring and loss of vision. Ocular infections with HSV are a major cause of blindness in North America. Immune responses play a major role in causing the tissue damage that results from recurrent ocular HSV infections, and T lymphocyte-mediated responses are a prominent cause of this damage. There is evidence that the CD8+ T cell subset is very important in these destructive immune responses (Hendricks, R. L., and Tumpey, M., *Contribution of virus and immune factors to herpes simplex virus type I-induced corneal pathology*, Invest. Opthalmol. Vis. Sci. 31:1929–1939 (1990)).

On initial infection, HSV usually produces a generalized, acute infection, which is cleared by the body's normal immune response. However, during the acute phase, some virus particles invade sensory nerve cells, and there they are able to become latent, and survive long after the acute infection has been cleared by the immune system, even though antibodies against them are abundant in the blood. They then later become re-activated and produce local infections. These are, as might be expected, fairly rapidly cleared by the already-prepared immune system. (Zweerink, H. J., and Stanton, L. W., *Immune response to herpes simplex virus infections: virus-specific antibodies in sera from patients with recurrent facial infections*, Infect. Immun. 31:624–630 (1981)). This cycle is quite familiar to those who are prone to "fever blisters", which appear to be caused by sunlight-induced activation of latent HSV particles in the lips.

Like certain other persistent viruses, it appears that HSV inhibits immune recognition of infected cells by interfering with the synthesis, transport or display of MHC class I complexes. One reason that this was not immediately appreciated by immunologists studying anti-HSV immunity is that in mouse models of HSV infection, the infected cells are primarily killed by HSV-specific CD8+ T lymphocytes, which specifically recognize MHC class I protein-HSV peptide complexes; this suggests that in these models, CD8+ T lymphocyte recognition is not strongly inhibited. However, in humans, the HSV-infected cells are more often specifically killed by HSV-specific T lymphocytes of another class, called CD4+, which recognize complexes composed of HSV-derived peptides and MHC class II proteins. (Schmid, D. S. and Rouse, B. T., *The role of T cell immunity in control of herpes simplex virus*, In: Herpes Simplex Virus: Pathogenesis, Immunobiology, and Control, B. T. Rouse, ed. (Berlin:Springer-Verlag) pp. 57–74 (1992). Furthermore, it has been found that human fibroblasts that are infected with HSV are not recognized and killed by HSV-specific CD8+ lymphocytes, but are killed by non-specific natural killer (NK) cells, which are not dependent on MHC class I complexes for recognition (Posavad, C. M. and Rosenthal, K. L., *Herpes simplex virus-infected human fibroblasts are resistant to and inhibit cytotoxic T-lymphocyte activity*, J. Virol. 66:6264–6272 (1992)). These findings suggest that recognition by CD8+ T lymphocytes is inhibited in human HSV infections.

Exactly what mechanism, what genes and what proteins might be involved in HSV's ability to suppress immune recognition has, until discovery of the present invention, remained unknown. HSV resistance to T lymphocyte recognition was known to occur within 2 to 3 hours of infection, id., but MHC class I expression on the surface of HSV-infected cells was not observed to be markedly reduced until 14–20 hours after infection (Carter, V. C., Jennings, S. R., Rice, P. L. and Tevethia, S. S., *Mapping of a herpes simplex virus type 2-encoded function that affects the susceptibility of herpes simplex virus-infected target cells to lysis by herpes simplex virus-specific cytotoxic T lymphocytes*, J. Virol. 49:766–771 (1984)). Furthermore, other cell-to-cell propagated inactivation mechanisms have also been observed (York, I., and Johnson, D. C., *Direct contact with herpes simplex virus-infected cells results in inhibition of lymphokine-activated killer cells due to cell to cell spread of virus*, J. Infect. Dis. 168:1127–1132 (1993)).

The genome of herpes simplex virus type 1 is encoded on a linear, double-stranded DNA of about 152 kilobases. The HSV-1 genome has been completely sequenced. See: McGeoch, D., M. A. Dalrymple, A. J. Davison, A. Dolan, M. C. Frame, D. McNab, L. J. Perry, J. E. Scott and P. Taylor, *The Complete DNA sequence of the Long Unique Region in the Genome of Herpes Simplex Virus Type* 1, J. Gen. Virol. 69: 1531–1574 (1988). The genome codes for about 76 proteins, many of which have been named according to when in the infectious cycle they are produced. The protein sequences for all of the HSV-1 proteins are known, having been deduced from their corresponding gene sequences. Furthermore, many years of research has resulted in the identification of the function for many of these proteins. Nevertheless, there are still a number of proteins encoded by the HSV-1 genome that have no known function.

One of the proteins whose function has remained unknown is the immediate-early protein ICP47. Various researchers have given this protein other names, including IE12, Vmw12, and IE5. The gene for this protein is known as US 12, and is also known as α47. The coding region of the US 12 gene is 264 base pairs long, which means that the ICP47 protein is 88 amino acids long. Although ICP47 is observed to migrate in gel electrophoresis as a protein of about 12,000 daltons, the molecular weight, as calculated from its amino acid sequence, is 9792 daltons (McGeoch, D.

J., Dolan, A., Donald, S., and Rixon, F. J., *Sequence determination and genetic content of the short unique region in the genome of herpes simplex virus type 1*, J. Mol. Biol. 181:1–13 (1985)).

Various researchers have previously attempted to discern the function of ICP47, but prior to the present invention, without success. Deletion of the US 12 gene has been found to have no effect on infectivity (Mavromara-Nazos, P., Ackermann, M., and Roizman, B., *Construction and properties of a viable herpes simplex virus 1 recombinant lacking coding sequences of the α47 gene*, J. Virol. 60:807–812 (1986)), and the most recent reported effort to determine the function of ICP47 concluded that the US 12 gene plays "no important role in the establishment and/or reactivation from latency" (Nishiyama, Y., Kurachi, R., Daikoku, T., and Umene, K., *The US9, 10, 11, and 12 genes of herpes simplex virus type 1 are of no importance for its neurovirulence and latency in mice*, Virology 194:419–423 (1993)).

Herpes Simplex Virus type 1 is but one member of an extended family of viruses. HSV type 2 is a close relative; its genome is "collinear" with that of HSV type 1, with "reasonable, but not identical, matching of base pairs". (Whitley, Supra at 1845). Other members of the human herpesvirus family include cytomegalovirus, varicella-zoster virus, herpes virus 6, herpes virus 7, and Epstein-Barr virus. There are also more than 50 herpesviruses that infect more than 30 other animal species (Id.), including some that infect humans.

Herpes Simplex Virus Type 2 has a gene that corresponds to the HSV Type 1 US 12 gene. It maps in the same genomic location, and produces a protein that migrates as a 12,300 dalton protein on gel electrophoresis, which is similar to the migration of ICP47 (Marsden, H. S., Lang, J., Davison, A. J., Hope, R. G., and MacDonald, D. M., *Genomic location and lack of phosohorylation of the HSV immediate-early polypeptide IE 12*, J. Gen. Virol. 62:17–27 (1982)). We have compared these gene sequences, and have determined that the Herpes Simplex Virus types 1 and 2 ICP47 proteins are 45% identical at the amino acid level, and 60% homologous when one allows substitution of similar amino acids.

Varicella-Zoster Virus does not appear to have a gene corresponding to US 12 (Davison, A. J., and D. J. McGeoch, *Evolutionary Comparisons of the S Segments in the Genomes of Herpes Simplex Virus Type 1 and Varicella-Zoster Virus*, J. Gen. Virol. 67:597–611 (1986)), and the pseudorabies virus does not appear to contain a sequence corresponding to US 12 in the region encoding genes corresponding to other "unique stretch" (US) genes (Zhang, G., and D. P. Leader, *The Structure of the Pseudorabies Virus Genome at the End of the Inverted Repeat Sequences Proximal to the Junction with the Short Unique Region*, J. Gen. Virol. 71:2433–2441 (1990)). However, it is unclear whether the many other herpesviruses contain such genes.

ADVANTAGES AND SUMMARY OF THE INVENTION

It is an object of the present invention to provide a method for introducing into cells an isolated gene or other protein coding nucleic acid sequence, the expression of which will at least partially interfere with one or more mechanism involved in specific recognition by T lymphocytes.

It is also an object of the present invention to provide a method for introducing into a virus an isolated gene or other protein coding nucleic acid sequence, the expression of which will reduce immune responses to the virus so that immune suppression or destruction of virus infected cells is reduced or delayed.

It is also an object of the present invention to provide a method for introducing into cells a protein that will at least partially interfere with one or more mechanism involved in specific recognition by T lymphocytes.

It is a further object of the present invention to provide a method of introducing into virus-infected cells a protein that will enable the virus to persist by at least partially avoiding recognition by T lymphocytes.

It is another object of the present invention to provide a new element for a gene therapy vector, and to provide an improved gene therapy vector.

It is also an object of the present invention to provide a method for the treatment of herpesvirus infections and to provide a method for the elimination of latent herpesviruses.

It is also an object of the present invention to provide a method for identifying drugs useful in the treatment of herpesvirus infections, and to provide drugs identified thereby.

An additional object of the present invention is to provide a method to suppress T lymphocyte-mediated organ or tissue transplant rejection.

Yet another object of the present invention is to provide a method for the treatment of T lymphocyte mediated autoimmune diseases.

Still another object of the present invention is to provide a method for the treatment of diabetes.

Another object of the present invention is to provide a method for the treatment of multiple sclerosis.

Yet another object of the present invention is to provide a method for the treatment of arthritis.

Another object of the invention is to provide a method for the prevention of tissue damage that occurs as a result of immune responses to ocular herpes infections.

According to an embodiment of the invention, a method for improving the infective persistence of a virus is described. This method comprises introducing into the viral genome an isolated nucleotide sequence encoding a protein selected from the group of ICP47 of HSV type 1, IE 12 of HSV type 2, proteins that are more than 40% homologous to ICP47 of HSV-1, and fragments of any of the foregoing that are able to improve said infective persistence.

According to another embodiment of the invention, a vector element able to suppress cell recognition by cytotoxic T lymphocytes by vector-infected cells is realized that comprises an isolated nucleotide sequence encoding a protein selected from the group of ICP47 of HSV type 1, IE 12 of HSV type 2, proteins that are more than 40% homologous to ICP47 of HSV-1, and fragments of any of the foregoing that are able to suppress said recognition.

According to yet another embodiment of the invention, a vector element able to suppress cell recognition by cytotoxic T lymphocytes by vector-infected cells is realized, which comprises an isolated nucleotide sequence selected from the group of the US 12 gene from HSV Type 1, the HSV Type 2 gene encoding the IE 12 protein, nucleic acid sequences that are more than 40% homologous to the Herpes Simplex Virus Type 1 US 12 gene, and fragments of any of the foregoing that are able to supress said recognition.

According to yet another embodiment of the invention, a vector element is realized that comprises the 714bp NruI-XhoI fragment of pRHP6, including part of the first exon, the intron, and the entire coding sequences of ICP47.

According to another embodiment of the invention, an adenovirus vector is realized, comprising an adenovirus having the identifying characteristics of AdICP47-1.

According to yet another embodiment of the invention, a method for inhibiting cell recognition by cytotoxic T lymphocytes is described, comprising introducing into cells an isolated nucleotide sequence encoding a protein selected from the group of ICP47 of HSV type 1, IE 12 of HSV type 2, proteins that are more than 40% homologous to ICP47 of HSV-1, and fragments of any of the foregoing that are able to inhibit said recognition.

According to another embodiment of the invention, a method for inhibiting cell recognition by cytotoxic T lymphocytes is described which comprises introducing into infected cells an isolated protein selected from the group of ICP47 of HSV type 1, IE 12 of HSV type 2, proteins that are more than 40% homologous to the ICP47 protein of HSV-1, and fragments of any of the foregoing that are able to inhibit said recognition.

According to yet another embodiment of the invention, a method for the treatment of herpesvirus infections is provided, which comprises the introduction into infected cells of a nucleotide sequence that is complementary to the mRNA sequence encoding a protein selected from the group of ICP47 of HSV type 1, IE 12 of HSV type 2, proteins that are more than 40% homologous to ICP47 of HSV-1, and biologically active fragments of any of the foregoing, wherein the complimentary portion of said nucleotide sequence is of sufficient length to inhibit the translation of said mRNA and thereby inhibit the production of said protein.

According to still another embodiment of the invention, a method for the treatment of herpesvirus infections is provided, which comprises the introduction into infected cells of an antibody specific for a protein selected from the group of ICP47 of HSV type 1, IE 12 of HSV type 2, proteins that are more than 40% homologous to ICP47 of HSV-1, and antigenic fragments of any of the foregoing.

According to yet another embodiment of the present invention, a method for identifying drugs useful in treating herpesvirus infections is provided, which comprises establishing a model cell system that expresses a protein that is selected from the group of ICP47 of HSV type I, IE 12 of HSV type 2, proteins more than 40% homologous to ICP47, and fragments of any of the foregoing that exhibit the functional characteristics of ICP47; adding amounts of candidate compounds to samples of said model cells; and testing said samples for a trait different from that observed in samples to which no such compound has been added, said trait being selected from the group of suppressed synthesis of the ICP47 homologue, decreased MHC class I protein processing, and increased CTL lysis.

According to a further embodiment of the invention, a method is provided for the prevention and treatment of autoimmune diseases, which comprises introducing into a patient's cells a biomolecule selected from the group of an isolated nucleotide sequence encoding ICP47 of HSV type 1, an isolated nucleotide sequence encoding IE 12 of HSV type 2, isolated nucleotide sequences encoding proteins that are more than 40% homologous to ICP47 of HSV-1, the protein ICP47, the protein IE 12, proteins that are more than 40% homologous to ICP47, and therapeutically effective fragments of any of the foregoing.

Another embodiment of the invention provides a method for the prevention and treatment of tissue and organ transplant rejection, comprising introducing into the cells of said tissue or organ a biomolecule selected from the group of an isolated nucleotide sequence encoding ICP47 of HSV type 1, an isolated nucleotide sequence encoding IE 12 of HSV type 2, isolated nucleotide sequences encoding proteins that are more than 40% homologous to ICP47 of HSV-1, the protein ICP47, the protein IE 12, proteins that are more than 40% homologous to ICP47, and therapeutically effective fragments of any of the foregoing.

Still another embodiment of the present invention is a method for the prevention and treatment of diabetes, which comprises introducing into the cells of a patient a biomolecule selected from the group of an isolated nucleotide sequence encoding ICP47 of HSV type 1, an isolated nucleotide sequence encoding IE 12 of HSV type 2, isolated nucleotide sequences encoding proteins that are more than 40% homologous to ICP47 of HSV-1, the protein ICP47, the protein IE 12, proteins that are more than 40% homologous to ICP47, and therapeutically effective fragments of any of the foregoing.

A further embodiment of the present invention is a method for the prevention and treatment of multiple sclerosis, comprising introducing into the cells of a patient a biomolecule selected from the group of an isolated nucleotide sequence encoding ICP47 of HSV type 1, an isolated nucleotide sequence encoding IE 12 of HSV type 2, isolated nucleotide sequences encoding proteins that are more than 40% homologous to ICP47 of HSV-1, the protein ICP47, the protein IE 12, proteins that are more than 40% homologous to ICP47, and therapeutically effective fragments of any of the foregoing.

An additional embodiment of the invention is a method for the prevention and treatment of arthritis comprising introducing into the cells of a patient a biomolecule selected from the group of an isolated nucleotide sequence encoding ICP47 of HSV type 1, an isolated nucleotide sequence encoding IE 12 of HSV type 2, isolated nucleotide sequences encoding proteins that are more than 40% homologous to ICP47 of HSV-1, the protein ICP47, the protein IE 12, proteins that are more than 40% homologous to ICP47, and therapeutically effective fragments of any of the foregoing.

Another embodiment of the present invention is a method for reducing immune reactions in ocular herpesvirus infections, comprising introducing into the ocular tissues of a patient a biomolecule selected from the group of an isolated nucleotide sequence encoding ICP47 of HSV type 1, an isolated nucleotide sequence encoding IE 12 of HSV type 2, isolated nucleotide sequences encoding proteins that are more than 40% homologous to ICP47 of HSV-1, the protein ICP47, the protein IE 12, proteins that are more than 40% homologous to ICP47, and therapeutically effective fragments of any of the foregoing.

DETAILED DESCRIPTION OF THE PREFERRED EMBODIMENTS

Figure 1A:
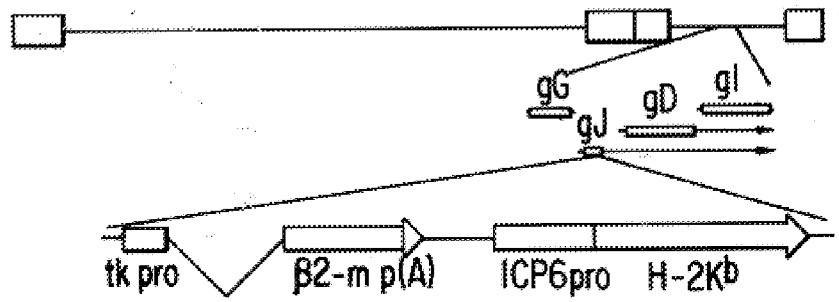
FIG. 1(A) is a diagram of the recombinant HSV-1 virus denoted F-US5MHC.

It is important to an understanding of the present invention to note that all technical and scientific terms used anywhere herein, unless otherwise defined, are intended to have the same meaning as commonly understood by one of ordinary skill in the art; that techniques employed herein are also those that are known to one of ordinary skill in the art, unless stated otherwise; and that publications mentioned herein are incorporated by reference.

It is also important to note that reference to particular DNA fragments, genes, cDNAs, mRNAs, complementary strands, protein expression products and the like, or to some subset of such related materials (e.g., reference to DNA, where other related materials are not specifically listed) is not intended to be limiting, but should be read to include all such related materials that one of ordinary skill in the art would recognize as being of interest or value in the particular context in which that discussion is presented. It is often possible to produce or procure a biomolecule that is structurally related to or derived from a stated material, and to use that biomolecule in a different but known procedure to achieve the same goals as those to which a the use of a suggested method, material or composition is directed. For example, it is often possible to use RNA instead of DNA to carry genetic information. It is also possible to use certain nucleic acid analogues in such applications. All such substitutions and modifications are included within the scope of the present invention.

It should also be noted that references to antibodies include both polyclonal and monoclonal antibodies, and also include sequences of nucleic acid that bind specifically to particular proteins of interest, which nucleic acids are referred to as "nucleic acid antibodies" (Gold, L., *Nucleic Acid Ligands*, PCT Application No. WO 91/19813, published Dec. 26, 1991).

Reference to a degree of homology between nucleic acids or proteins means the percentage of nucleic acid bases or amino acids that are located identically in the sequences being compared, as is commonly understood by those of ordinary skill in the art, unless it is specified that similar amino acids should be allowed. Where specified, allowing similar amino acids to be substituted means that hydrophobic amino acids may be substituted for one another, as may cationic amino acids be substituted for one another, etc., etc. Furthermore, in either case, although degrees of homology may be stated specifically, e.g., 40%, they are meant to include further levels of homology, e.g, 45%, 50%, 55%, 60%, 65%, 70%, 75%, 80%, 85%, 90% 95% and 100% Any mention of nucleic acid sequences encoding ICP47 or homologous proteins is intended to include all possible sequences of nucleic acids that might encode such proteins, and is not intended to be limited to the sequences derived from biological sources. Where no specific degree of homology is specified, the term "homologous" means having at least a 25% degree of homology.

In addition, when homologues of ICP47 are mentioned, it is not intended that this be limited to those homologues that occur in nature; as is known to those skilled in the art, by using modern molecular biological techniques of site-directed mutagenesis, vector expression and the like, it is possible to produce new polypeptides, and the nucleic acid sequences that encode them, that are homologous to ICP47 and its coding sequence to various levels and in tremendously varied specific ways. It is intended that such constructs, as well as the homologues that occur in nature, be included within the scope of this invention.

It should furthermore be understood that the scope of the present invention is not limited to full-length sequences of each of the nucleic acid and amino acid sequences described. As is well understood by those skilled in the art, it is often possible to prepare subfragments of those sequences, and for those subfragments, even small ones, to retain some or all of the biological activity of the full-length sequences. Such subfragments are included within the scope of this invention.

The terms "virus" and "vector" as used herein are not intended to be mutually exclusive; to the contrary, they overlap considerably. A vector often is properly termed a virus, as that term is commonly understood. A vector often is simply a virus that has had a genetic element added, and both the term virus and the term vector would properly apply. However, a vector may have a form other than that of a virus. In addition, it is not intended that the term virus only mean replicating virus particles; the term is intended, for example, to include non-replicating virus particles, portions of viruses, and bacterial plasmids.

The term "heavy chain" is equivalent to the term "MHC class I α-chains"; H-2K$^b$ is a specific heavy chain derived from a particular strain of mouse.

Experimental Procedures

Cells and Viruses

Many of the cell types used were of a common type, and are commercially available. Some cells used were obtained commercially, and others were obtained from various laboratories. The types of cells used, the non-commercial sources from which they were obtained (if any), and some key references in which they are described are listed below:

Vero (African Green Monkey kidney) cells;

R-970-5 human osteosarcoma cells (Rhim, J. S., Cho, H. Y., and Huebner, R. J., *Non-producer human cells induced by murine sarcoma cells*, Int. J. Cancer 15:23–29(1975)), were obtained from K. Huebner and C. Croce of the Wistar Institute, Philadelphia, Pa.;

MC57 cells, which are mouse fibrosarcoma cells of the H-2$^b$ haplotype (Zinkernagel, R. M., Adler, B., and Holland, J. J. *Cell-mediated immunity to vesicular stomatitis virus infections in mice*, Exp. Cell Biol. 46:53–70 (1978)) were obtained from M. Buchmeier of the Scripps Institute, La Jolla, Calif.;

B6/WT-3 cells, which are mouse cells of the H-2$^b$ haplotype (Pretell, J., Greenfield, R. S., and Tevethia, S. S., *Biology of simian virus 40 (SV40) transplantation antigen (TAg). V. In vitro demonstration of SV40 TAg in SV40 infected nonpermissive mouse cells by the lymphocyte mediated cytotoxicity assay*, Virology 97:32–41(1979)) were obtained from S. Tevethia at the University of Pennsylvania, Hershey, Pa.;

SVBALB cells, which are mouse cells of the H-2K$^d$ haplotype (Gooding, L. R., *Specificities of killing by T lymphocytes generated against syngeneic SV40 transformants: studies employing recombinants within the H-2 complex*, J. Immunol. 122:1002–1008 (1979)), were obtained from K. Rosenthal at McMaster University, Hamilton, Ontario, Canada;

Daudi cells, which are EBV-transformed human lymphoblastoid cells in which the β$_2$m genes are not expressed, (Klein, E., Klein, G., Nadkarni, J. S., Nadkarni, J. J., Wigzell, H., and Clifford, P., *Surface IgM-kappa specificity on a Burkitt lymphoma cell in vivo and in derived cell lines*, Cancer Res. 28:1300–1310 (1968));

293 cells, (Graham, F. L., Smiley, J., Russell, W. C., and Nairn, R., *Characteristics of a human cell line transformed by DNA from human adenovirus 5 DNA*. J. Gen. Virol. 36:59–74 (1977));

Normal human fibroblasts denoted gwfb, derived from a skin biopsy (used between passages 10–20), EBV-transformed lymphoblastoid cell lines, obtained from K. Rosenthal of McMaster University, Hamilton, Ontario, Canada;

The human CD8+ CTL clone, MR-16E6, which is specific for human cytomegalovirus (HCMV) phosphoprotein 65, was isolated and propagated as previously described (Riddell, S. R. and Greenberg, P. D., *The use of anti-CD3 monoclonal antibodies to clone and expand human antigen-specific T cells*, J. Immunol. Methods 128:189–201 (1990); Riddell, S. R., Watanabe, K. S., Goodrich, J. M., Li, C. R., Agha, M. E., and Greenberg, P. D., *Restoration of viral immunity in immunodeficient humans by the adoptive transfer of T cell clones*, Science 257: 238–257 (1992)).

Each of the forgoing cell strains were passaged in alpha-minimal essential media (α-MEM) containing 5 to 10% fetal bovine serum (FBS), unless otherwise indicated.

Many of the viruses used were also of a common type, and are commercially available. Some viruses used were obtained commercially, and others were obtained from various laboratories. The types of viruses used, the non-commercial sources from which they were obtained (if any), and some key references in which they are described are listed below:

HSV-1 strain F (Ejercito, P. M., Kieff, E. D., and Roizman, B., *Characterization of herpes simplex virus strains differing in their effect on social behaviour of infected cells*, J. Gen.Virol. 2:357–64 (1968)) was obtained from P. G. Spear at Northwestern University;

HSV-1 strain KOS (Smith, K. O., *Relationships between the envelope and the infectivity of herpes simplex virus*, Proc. Soc. Exp. Biol.Med. 115:814–16 (1964)) was also obtained from P. G. Spear at Northwestern University;

HSV-2 strain 333 (Kit, S., Kit, M., Qavi, H., Trkula, D., and Otsuka, H., *Nucleotide sequence of the herpes simplex virus type 2 (HSV-2) thymidine kinase gene and predicted amino acid sequence of the thymidine kinase polypeptide and its comparison with the HSV-1 thymidine kinase gene*, Biochim. Biophys. Acta 741:158–170 (1983)) was also obtained from P. G. Spear at Northwestern University;

The HSV-1 deletion mutant VhsB, lacking the vhs gene UL41 (Smibert, C. A., and Smiley, J. R., *Differential regulation of endogenous and transduced β-globin genes during infection of erythroid cells with a herpes simplex type 1 recombinant*, J. Virol. 64:3882–94 (1990)) was obtained from J. Smiley at McMaster University, Hamilton, Ontario, Canada;

The HSV-2 mutant lacking the vhs gene (Smibert and Smiley, unpublished) was also obtained from J. Smiley at McMaster University, Hamilton, Ontario, Canada;

The ICP0 deletion mutant, dlx3.1, (Sacks, W. R., and Schaffer, P. A., *Deletion mutants in the gene encoding the herpes simplex virus type 1 immediate-early protein ICP0 exhibit impaired growth in cell culture*, J. Virol. 61:829–839 (1987)) was obtained from P. Schaffer at the Dana-Farber Institute, Boston, Mass.;

The ICP22 deletion mutant, R325-βT$^+$, (Sears, A. E., I. W. Halliburton, B. Meignier, S. Silver, and B. Roizman, *Heroes simplex virus 1 mutant deleted in the α22 gene: growth and gene expression in permissive and restrictive cells and establishment of latency in mice*. J. Virol. 55:338–346 (1985)) was obtained from B. Roizman at the University of Chicago;

The ICP6 deletion mutant, ICP6Δ, (Goldstein, D. J., and Weller, S. K., *An ICP6::lacZ insertional mutagen is used to demonstrate that the UL52 gene of herpes simplex virus type 1 is required for virus growth and DNA synthesis*, J. Virol. 62:2970–2977 (1988)) was supplied by S. Weller of the University of Connecticut, Farmington, Conn.;

The ICP47 mutant, N38, (Umene, K., *Conversion of a fraction of the unique sequences to part of the inverted repeats in the S component of the herpes simplex virus type 1 genome*, J. Gen. Virol. 67:1035–1048 (1986)) was obtained from K. Umene at the Kyushu University, Fukuoka, Japan;

The HSV-1 ICP4-mutant, d120, was propagated on complementing E5 cells (DeLuca, N. A., McCarthy, A. M., and Schaffer, P. A., *Isolation and characterization of deletion mutants of herpes simplex virus type 1 in the gene encoding immediate-early regulatory protein ICP4*, J. Virol. 56:558–570 (1985)), and was obtained from P. Schaffer at the Dana-Farber Institute, Boston, Mass.;

The HSV-1 ICP27 deletion mutant, 5dl.1.2, was propagated on complementing 3-3 cells (McCarthy, A. M., McMahan, L., and Schaffer, P. A., *Herpes Simplex virus type 1 ICP47 deletion mutants exhibit altered patterns of transcription and are DNA deficient*, J. Virol. 63:18–27 (1989)) was also obtained from P. Schaffer at the Dana-Farber Institute, Boston, Mass.;

The HSV-1 gD$^-$ mutant F-US6kan was grown on complementing VD60 cells (Ligas, M. W., and Johnson, D. C. *A herpes simplex virus mutant in which glycoprotein D sequences are replaced by β-galactosidase sequences binds to but is unable to penetrate into cells*, J. Virol. 62:1486–94 (1988)).

Unless otherwise specified, and all the foregoing viruses were propagated and titered on Vero cells.

Plasmids, viral DNA and Vectors

Many of the plasmids used were of a common type, and are commercially available. Some plasmids used were obtained commercially, and others were obtained from various laboratories. These plasmids, the non-commercial sources from which they were obtained (if any), and some key references in which they are described are listed below:

Plasmid pTK173, containing the HSV-1 thymidine kinase gene (Smiley, J. R., Swan, H., Pater, M. M., Pater, A., and Halpern, M. E., *Positive control of the herpes simplex virus thymidine kinase gene requires upstream DNA sequences*, J. Virol. 47:301–310 (1983)) was obtained from J. Smiley at McMaster University, Hamilton, Ontario, Canada;

Plasmid pD6p, containing a lacZ gene cassette under control of the HSV-1 ICP6 promoter (Goldstein, D. J., and Weller, S. K., *An ICP6::lacZ insertional mutagen is used to demonstrate that the UL52 gene of herpes simplex virus type 1 is required for virus growth and DNA synthesis*, J. Virol. 62:2970–2977 (1988)) was obtained from S. Weller of the University of Connecticut, Farmington, Conn.;

Plasmid pcKb, containing a EcoRI fragment including the murine H-2K$^b$ gene inserted into plasmid pUC19 (Schönrich, G., Kalinke, U., Momburg, F., Malissen, M., Schmitt-Verhulst, A. M., Mallissen, B., Hammerling, G. J., and Arnold, B., *Down-regulation of T cell receptors on self-reactive T cells as a novel mechanism for extrathymic tolerance induction*, Cell 65:293–304 (1991)) was obtained from W. Jefferies at the University of British Columbia, Vancouver, British Columbia;

Plasmid pVc β2, containing the "a" allelle of murine β-microglobulin gene under the control of the SV40 promoter (Daniel, F., Morello, D., Le Bail, O., Chambon, P., Cayre, Y., and Kourilsky, P., *Structure and expression of the mouse β2-microglobulin gene isolated from somatic and non-expressing teratocarcinoma cells*, EMBO J. 2:1061–1065 (1983)), was also obtained from W. Jefferies at the University of British Columbia;

Plasmid pRHP6, containing ICP4 and ICP47 sequences from HSV-1(KOS) (Perrson, R. H., Bacchetti, S., and Smiley, J. R., *Cells that constitutively express the herpes simplex virus immediate-early protein ICP4 allow efficient activation of viral delayed-early genes in trans*, J. Virol. 54:414–421 (1985)), was obtained from S. Bacchetti at McMaster University, Hamilton, Ontario, Canada;

Plasmid pS456, which contains a BamHI-MscI fragment derived from plasmid pSS17 (Johnson, D. C., Frame, M. C., Ligas, M. W., Cross, A. M., and Stowe, N. D., *Herpes simplex virus immunoglobulin G Fc receptor activity depends on a complex of two viral glycoproteins, gE and gI*, J. Virol. 61:2208–2216 (1988));

HSV-1 gD-mutant F-US6KAN (Smiley, J. R., Fong, B., and Leung, W.-C., *Construction of a double jointed herpes simplex virus DNA molecule: inverted repeats are required for segment inversion and direct repeats promote deletions*, Virology 113:345–362 (1981)).

Still other plasmids, viral DNA and vectors used in the experiments described herein were produced by recombinant DNA techniques that are well known in the art (Sambrook, J., Fritsch, E. F., and Maniatis, T., *Molecular Cloning, a Laboratory Manual,* 2nd Ed., Cold Spring Harbor Press, 1989), and were prepared as follows:

To construct the recombinant HSV-1 expressing murine MHC class I proteins, the 2.2 kb BamHI-NruI fragment from pVcβ2 containing the β2-microglobulin gene was subcloned adjacent to the thymidine kinase promoter from pTK173 and the 1.2kb SalI-PvuII fragment of pcKb containing the murine H-2K$^b$ gene was placed under the control of the ICP6 promoter from pD6p. These β2-microglobulin/TK and H-2K$^b$/ICP6 genes were then inserted into a unique NruI site in the US5 gene of pS456, producing pS5MHC. pS5gal was produced by insertion of the 4.7 kb BamHI fragment containing the ICP6::lacZ cassette from pD6p into the NruI site in pS456.

Infectious viral DNA was prepared from Vero cells infected with the HSV-1 gD-mutant F-US6KAN. Vero cells were co-transfected with F-US6KAN DNA and either plasmid pS5MHC or pS5gal, producing the viral recombinants F-US5MHC or F-US5β, respectively, as previously described (Johnson, D. C., and Feenstra, V., *Identification of a novel herpes simplex vitus type 1-induced glycoprotein which complexes with gE and binds immunoglobulin*, J. Virol. 61:2208–2216 (1987)). Recombinant viruses were repeatedly plaque purified on Vero cells, in which parental F-US6KAN cannot replicate.

To construct an adenovirus vector expressing ICP47, designated AdICP47-1, the 714bp NruI-XhoI fragment of pRHP6, including part of the first exon, the intron, and the entire coding sequences of ICP47, was inserted into the EcoRV - SalI region of pCA4 (C. Addison and F. L. Graham, unpublished), which contains the left side of the adenovirus type 5 genome with a deletion spanning the E1 region, into which is inserted the human cytomegalovirus (HCMV) immediate early promoter, a polylinker, and the SV40 polyadenylation signal, so that the ICP47 coding sequences were placed next to the HCMV promoter; this produced the plasmid p47NXE1. p47NXE1 was co-transfected with plasmid pBHG10, which contains full-length adenovirus 5 sequences but without the packaging signal at the leftward side of the Ad5 genome (A. Bett and F. L. Graham, unpublished) into 293 cells. Recombinant adenoviruses, in which the ICP47/HCMV promoter cassette was inserted in the E1 region and containing a deletion in the E3 region, were plaque purified on 293 cells and viral DNA was examined by restriction enzyme analysis.

Similarly, the control adenovirus vector AddlE1 was constructed by rescuing the plasmid pCA4 with the plasmid pJM17 (McGregory, W. J., Bautista, D. S., and Graham, F. L., A simple technique for the rescue of early region I mutations int infectious human adenovirus type 5, Virology 163:614–617 (1988)). The resulting virus lacked the same E1 and E3 sequences as AdICP47-1, but did not encode ICP47 or any other foreign gene.

UV-inactivation of HSV

HSV-2(333) or HSV-2 (333 vhs–) virus stocks were prepared by suspending Vero cells in PBS containing 1% FBS, sonicating the cells extensively, and centrifuging the material at 1000×g for 10 minutes to remove insoluble material. The viruses were then diluted in PBS containing 1% FBS to 2 to 3 ml, placed in a 60 mm dish and subjected to UV light (3 joules/cm$^2$/sec using a bacteriostatic fluorescent tube) for 2 minutes with constant stirring while on ice. UV-inactivated viruses were shown to be unable to express any viral proteins by immunoprecipitation and Western blotting; the 333 stock retained vhs activity.

Antibodies

Antibodies used, their sources, and key references describing them are:

A hybridoma expressing monoclonal antibodies Y3, which reacts with H-2K$^b$ complexed with $\beta_2$-microglobulin, (Jones, B., and Janeway, C. A., Jr., *Cooperative interaction of B lymphocytes with antigen-specific helper T lymphocytes is MHC restricted*, Nature 292:547–549 (1981)) were obtained from the American Type Culture Collection (ATCC), Bethesda, Md.;

A hybridoma expressing monoclonal antibody W6/32 (Parham, P., Barnstable, C. J., and Bodmer, W. F., *Use of a monoclonal antibody (W6/32) in structural studies of HLA-A,B,C antigens*, J. Immunol. 123:342–349 (1979)), which reacts with HLA-A, B, or C complexed with $\beta_2$-microglobulin, was also obtained from ATCC;

Rabbit antiserum raised against a peptide from exon 8 of H-2K$^b$ (Smith, M. H., Parker, J. M. R., Hodges, R. S., and Barber, B. H., *The preparation and characterization of anti-peptide heteroantisera recognizing subregions of the intracytoplasmic domain of class I H-2 antigens*, Mol. Immunol. 23:1077–1092 (1986)), which reacts with H-2K$^b$ either complexed with, or free of, $\beta$2-microglobulin, was provided by B. Barber of the University of Toronto, Toronto, Canada;

Monoclonal antibody HC10, which reacts with unfolded human HLA-B and C α-chains, and certain HLA A types (Stam, N. J., Spits, H., and Ploegh, H. L., *Monoclonal antibodies raised against denatured HLA-B locus heavy chains permit biochemical characterization of certain HLA-C locus products*, J. Immunol. 137:2299–2306 (1986)), was provided by H. Ploegh at the Massachusetts Institute of Technology (MIT) in Boston, Mass.;

A rabbit antiserum raised to human: $\beta_2$m, which cross-reacts with mouse $\beta_2$m, was obtained from Dakopatts of Copenhagen, Denmark;

A rabbit polyclonal antiserum directed against peptide corresponding to the C-terminus of ICP47 (Palfreyman, J. W., MacLean, J. B., Messeder, E., and Sheppard, R. C. *Successful use of oligopeptides as immunogens in the preparation of antisera to immediate-early gene products of herpes simpex virus type 1*, J. Gen. Virol. 65:865–874 (1984)) was obtained from H. Marsden at the Institute for Virology, Glasgow;

LP2, a monoclonal antibody specific for HSV gD (Minson, A. C., Hodgman, T. C., Digard, P., Hancock, D. C., Bell, S. E., and Buckmaster, E. A., *An analysis of the biological properties of monoclonal antibodies against glycoprotein D of heroes simplex virus and identification of amino acid substitutions that confer resistance to neutralization*, J. Gen. Virol. 67:1001–1013 (1986)) was a gift of A. C. Minson at Cambridge University, Cambridge, England;

T56/14, a monoclonal antibody specific for the transferrin receptor, was obtained from Oncogene Science, Uniondale, N.Y.

Radiolabeling of cells, immunoprecipitations, and endoglycosidase H digestions

Human fibroblasts or Daudi cells were metabolically labeled with $^{35}$S-methionine and $^{35}$S-cysteine as previously described (Johnson, D. C., and Feenstra, V., *Identification of a novel herpes simplex vitus type 1induced glycoprotein which complexes with gE and binds immunoglobulin*, J. Virol. 61:2208–2216 (1987)). For pulse-chase experiments, 100 mm plates of fibroblasts were labeled for 20–30 minutes with 100, μCi/ml each of $^{35}$S-methionine and $^{35}$S-cysteine (Dupont, Dorval, Quebec) then cell extracts were made using 1% Nonidet P40, 0.5% sodium deoxycholate, 50 mM Tris-HCl, ph 7.5, 100 mM NaCl (NP40/DOC buffer) containing 2 mg/ml bovine serum albumin (BSA), and 1 mM phenyl methylsulfonyl fluoride (pulse) or cells were washed and incubated in alpha-MEM containing 1% FBS for 90 minutes then cell extracts were made (chase).

Immunoprecipitations were carried out as described previously (Id.). Cell extracts were stored overnight at −70° C. and were then clarified by centrifugation at 87,000×g for 1 hr, then were mixed with ascites fluids or serum and incubated on ice for 1–1.5 Extracts to be immunoprecipitated with monoclonal antibody HC10 were first heated at 70° C. for 1 hour to partially denature MHC class I molecules, and then the extracts were cooled on ice. This treatment increased the fraction of class I molecules precipitated with HC10. Protein A-Sepharose was added and incubated a further 1.5–2 hours with mixing. The protein A beads were collected by centrifugation, washed 3–4 times with NP40/DOC buffer, and proteins were eluted by adding one volume of 2×loading buffer (40% SDS, 20% glycerol, 40% β-mercaptoethanol and bromophenol blue) to each volume of beads and heating the beads at 100° C. for 5–10 minutes. The stability of the MHC class I protein complex was determined by first labeling class I proteins in uninfected or HSV-1 (Vhs-B)-infected fibroblasts using $^{35}$S-methionine and $^{35}$S-cysteine (100 uCi/ml) for 1 hour, then chasing the label for 30 minutes. Cell extracts were made using NP40/DOC buffer containing 5 mg/ml BSA and 120 TIU/ml aprotinin, and these extracts were incubated for 1 hour or 18 hours on ice and then immunoprecipitated using monoclonal antibodies W6/32 or HC10.

Endoglycosidase H (endo H) digestions were performed with extracts from cells that had been labeled using a pulse-chase protocol. MHC class I, gD or transferrin receptors were immunoprecipitated using the appropriate antibodies, and proteins were eluted by suspending the samples in denaturing buffer (0.5% SDS, 1% β-mercaptoethanol) and boiling them for 10 minutes. Half of each eluted protein sample was treated with 1000 U endo H (New England Biolabs, Mississauga, Ontario, Canada) in reaction buffer (50 mM sodium citrate) and half was incubated in reaction buffer alone, both for 3 hours at 37° C. The eluted proteins were then subjected to electrophoresis through 14% polyacrylamide gels for MHC class I proteins and through 8.5% polyacrylamide gels for gD and the transferrin receptor. The gels were impregnated with Enlightening (New England Nuclear, Boston, Mass.) and exposed to X-ray film or read using a phosphorImager (Molecular Dynamics, Sunnydale, Calif.).

Cytotoxic T Lymphocyte lysis assays

Cytotoxic T Lymphocyte (CTL) lysis assays involving mouse cells were performed essentially as previously described (Pfizenmaier, K., Jung, H., Starzinski-Powitz, A., Rollinghoff, M., and H. Wagner, *The role of T cells in anti-herpes simplex virus immunity. I. Induction of antigen-specific cytotoxic T lymphocytes*, J. Immunol. 119:939–944 (1977)). Briefly, C57BL/6 (H-2K$^b$) or BALB/c (H-2K$^d$) mice were infected with 1×10$^6$ PFU of virus in the hind footpad. After 5 days, the mice were anesthetized and killed, and popliteal lymph nodes were removed and crushed through stainless steel mesh. The lymphocytes were cultured for 3 days at 37° C. in RPMI 1640/10% FCS/5×10$^{-5}$ mM β-mercaptoethanol (CTL medium). HSV-infected target cells (1–2×10$^4$ cells in 200 ml αMEM) were added to each well of a 96-well plate, the cells were labeled with $^{51}$Cr (Hanke, T., Graham, F. L., Rosenthal, K. L., and Johnson, D. C., *Identification of an immunodominant cytotoxic T-lymphocyte recognition site in glycoprotein B or herpes simplex virus by using recombinant adenovectors and synthetic peptides*, J. Virol. 65:1177–1186 (1991)), and CTLs were added at various effector:target cell ratios to a total of 200 ml CTL medium, and were incubated for 4 hours at 37° C.

Cytotoxic T lymphocyte lysis assays involving human cells were performed using a human CD8+ CTL clone, MR-16E6, which is specific for human cytomegalovirus (HCMV) phosphoprotein 65. Human fibroblasts were infected with a recombinant adenovirus vector, AdICP47-1 or AddlE1, for 36 hours, then were subsequently infected with HCMV for 12 hours. They were then labeled with $^{51}$Cr, mixed with the CTL clone using various effector to target (E:T) ratios, and were incubated for 5 hours at 37° C.

The results of the CTL lysis assays were determined by removing and counting 100 μl from each well to obtain experimental release (ER) of $^{51}$Cr. Maximum release (MR) was obtained by counting aliquots after treatment with 1M HCl. In each case samples were counted in a gamma radiation counter. Total release (TR) was calculated using the equation TR=MR+0.5 ER. Non-specific release (NR) was determined using cells to which no effectors had been added. Specific release (SR) was calculated using the equation SR=(ER-NR)/(TR-NR).

Results and Conclusions

Figure 1B:
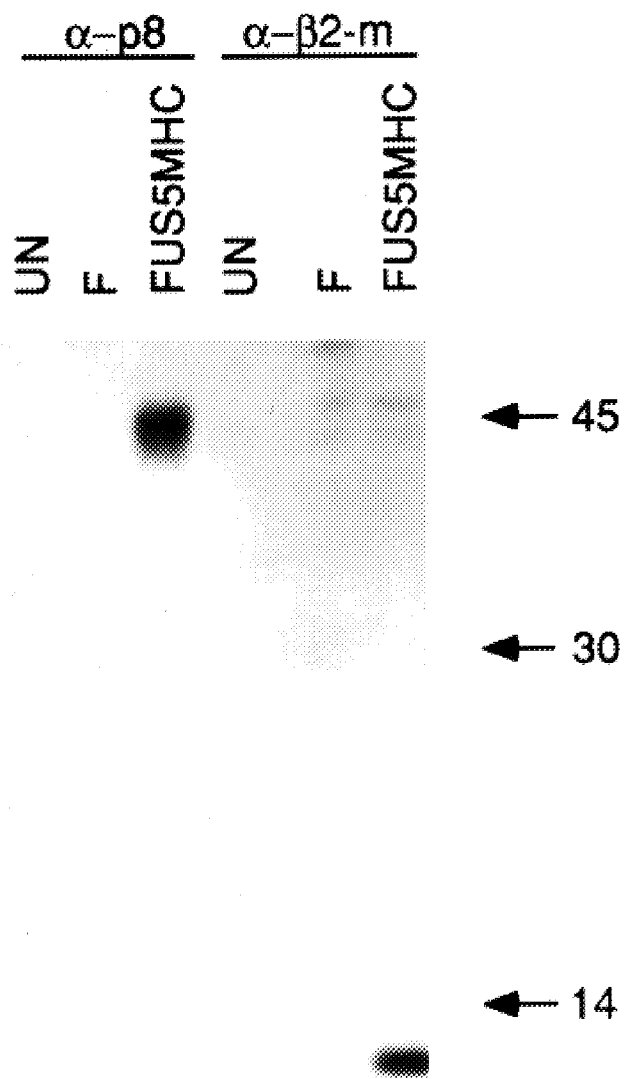
FIG. 1(B) is an autoradiogram of electrophoretically separated $^{35}$S cysteine-labeled proteins that were expressed by uninfected Daudi cells, Daudi cells infected with recombinant F-US5MHC, and Daudi cells infected with wild-type strain HSV-1(F), and which were purified by immune precipitation with rabbit anti-peptide 8 ($\alpha$-p8) antiserum and rabbit anti-$\beta$2-m antiserum ($\alpha$-$\beta$2-m)

Evidence that HSV-induced inhibition of MHC Class I complex presentation is not caused by blocking synthesis of MHC proteins, and is species-specific but not MHC class I-specific Previous observations that human CD8+ CTL were not able to lyse HSV-infected human fibroblasts and other normal diploid cells, e.g. keratinocytes (Posavad, C. M. and Rosenthal, K. L., 1992, Supra) suggested that these cells were not recognized by CTL. To examine this further with well-characterized murine CD8+, HSV-specific CTL, we constructed a recombinant HSV-1, F-US5MHC, which expresses murine MHC (H-2$^b$) class I molecules. In this construct, the murine H-2K$^b$ gene was placed under control of the HSV-1 ICP6 promoter, and the murine μ2-microglobulin gene was coupled to the HSV-1 thymidine kinase (tk) promoter; both of these constructs were then inserted into the HSV-1 US5 (gJ) gene, which is not required for virus replication. The structure of this clone is diagrammed in FIG. 1(A). We also constructed a control virus, F-US5β, where the HSV-1 US5 gene was interrupted with the ICP6::lacZ cassette from pD6p (Goldstein and Weller, 1988, Supra). Expression of the H-2K$^b$ and β$_2$-microglobulin proteins was then investigated by infecting Daudi cells, which do not express β$_2$-microglobulin, with F-US5MHC, with wild type HSV-1 strain F, or by leaving the cells uninfected (UN). Three hours after infection the cells were labeled with $^{35}$S-methionine and $^{35}$S-cysteine for 2 hours, and then cell extracts were made, and the H-2K$^b$ α-chain was immunoprecipitated using a rabbit anti-peptide 8 (α-p8); or, the β$_2$-microglobulin protein was immunoprecipitated using a rabbit anti-β2-m antiserum (α-β2-m). The results are shown in FIG. 1(B); molecular mass markers are shown on the right. Expression of both the H-2$^b$ α-chain and murine β2-microglobulin was detected in F-US5MHC-infected human Daudi cells, which do not normally express β2-microglobulin, but not in Daudi cells infected with wild-type HSV type 1 strain F (lanes marked "F"). Other experiments confirmed that the H-2K$^b$ α-chain was expressed in human fibroblasts and a number of other human cell types infected with F-US5MHC, and that this heavy chain protein reacted with the anti-H2K$^b$ conformation-dependent monoclonal antibody Y3 (data not shown).

Figure 2A:
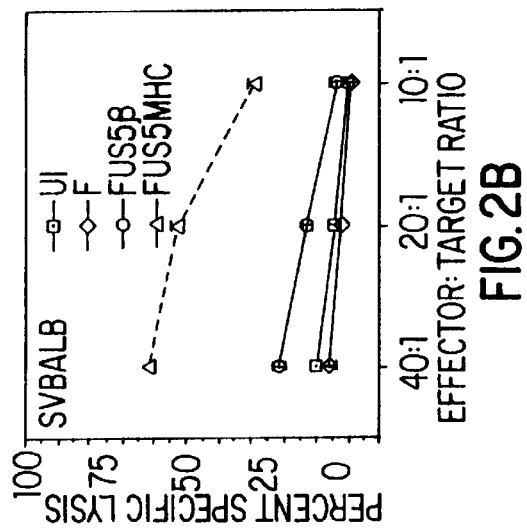
FIGS. 2(A), 2(B), and 2(C) show results of HSV-1-specific cytotoxic T lymphocyte lysis assays on 2(A) mouse fibrosarcoma (MC57) cells, 2(B) murine SVBALB cells, or 2(C) normal human fibroblasts (gwfb), each having first been infected with wild type HSV-1 (F), control virus FUS5 $\beta$, or F-US5MHC.
Figure 2B:
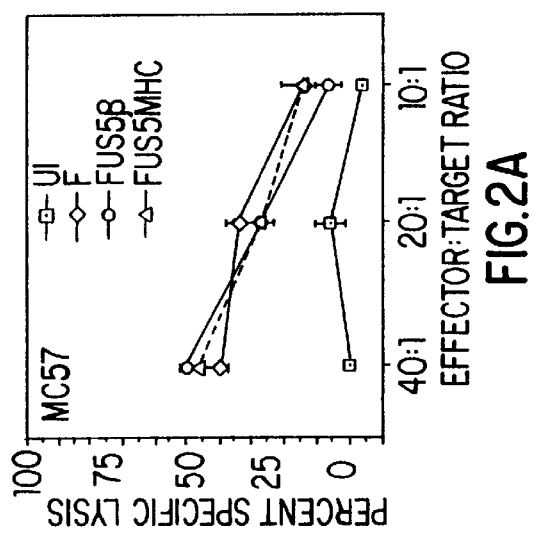
Figure 2C:
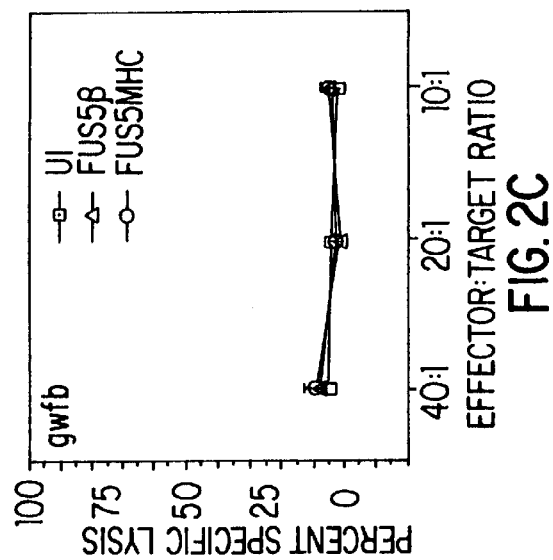

F-US5MHC should in theory render any cell susceptible to lysis by murine, H-2$^b$-restricted CTL. FIG. 2 shows that when cytotoxic T lymphocytes (CTL) derived from C57BL/6 mice (H-2$^b$) infected with HSV-1 (F) were used in CTL assays using effector to target ratios of 40, 20, or 10:1, mouse fibrosarcoma H-2$^b$ (MC57) target cells infected with F-US5MHC were efficiently lysed (FIG. 2(A)), as were (murine H-2$^d$) SVBALB cells (FIG. 2(B)). However, uninfected (UI) MC57 cells were not lysed (FIG. 2(A)), nor were uninfected SVBALB cells or SVBALB cells infected with wild type HSV-1 (F) or infected with control virus F-US5β. In other experiments, rat cells infected with F-US5MHC were also rendered susceptible to lysis by H-2$^b$-restricted CTL (data not shown). In contrast, normal human fibroblasts (gwfb) (FIG. 2(C)) and a panel of other human cells (data not shown) were not lysed by HSV-specific, H-2$^b$-restricted CTL after infection with F-US5MHC; nor were uninfected (UI) human normal fibroblasts or fibroblasts infected with F-US5β or F-US5MHC. Therefore, these human cells were not recognized by mouse cytotoxic T lymphocytes even though they expressed mouse MHC class I molecules. Together these results suggest that the HSV-induced inhibition of presentation to CTL is not related to inhibition of MHC class I synthesis and may be species-specific, but is not MHC class I-specific.

Figure 3A:
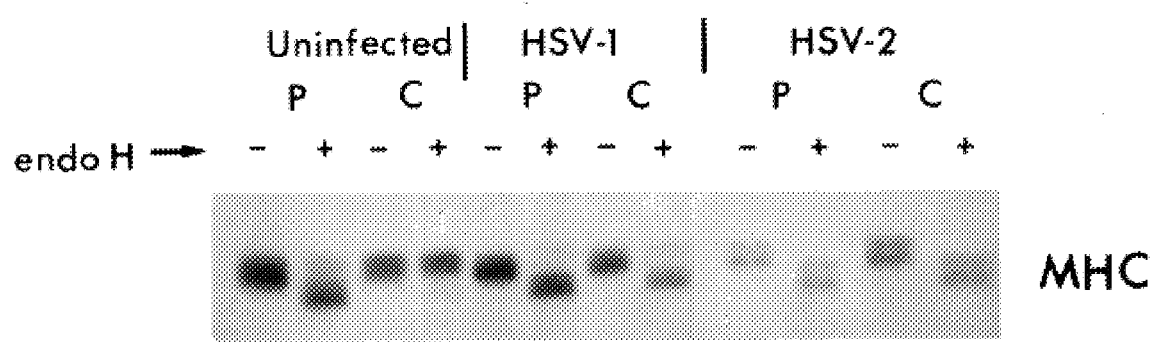
FIGS. 3(A), 3(B), 3(C), and 3(D) show autoradiograms of electrophoretically separated products from pulse-chase experiments where 2(A) MHC class 1 α chain proteins, 3(B) HSV-1 or HSV-2 glycoprotein D (gD), and 3(C) the transferrin receptor were immunoprecipitated using monoclonal antibodies, and 3(D) samples either were or were not treated with endoglycosidase H digestion prior to electrophoresis.
Figure 3B:
Figure 3C:
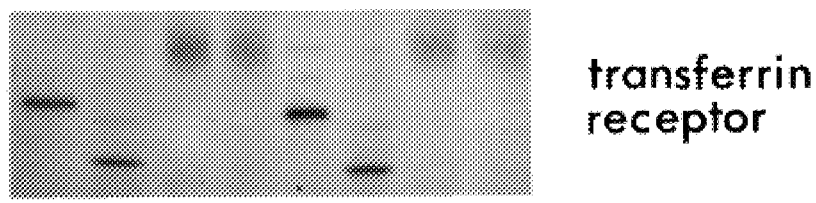
Figure 3D:
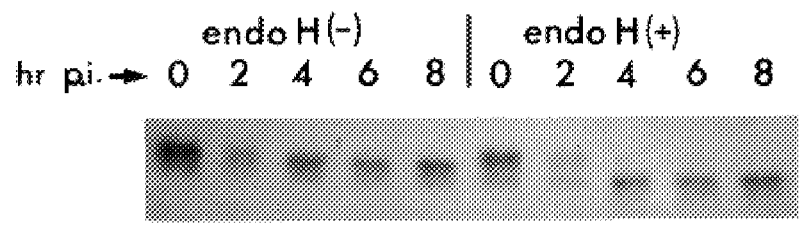

Evidence that MHC class I molecules in HSV-infected cells are retained within the ER/cis Golgi compartment To further study MHC class I molecules in HSV-infected human cells, we used a pulse-chase protocol to examine intracellular transport and processing of class I α-chain molecules. Normal human fibroblasts (gwfb) were left uninfected or were infected with HSV-1(KOS) or HSV 2(333) for 3 hr, then labeled with $^{35}$S-methionine and $^{35}$S-cysteine for 30 minutes and lysed (pulse: P) or the label was chased for 90 minutes (chase: C) before lysis. The results are shown in FIG. 3. In FIG. 3(A), MHC class 1 βchain proteins were immunoprecipitated using monoclonal antibody HC10; in FIG. 3(B), HSV-1 or HSV-2 glycoprotein D (gD) were immunoprecipitated using monoclonal antibody LP2; and in FIG. 3(C), the transferrin receptor was immunoprecipitated using the monoclonal antibody T56/14. The proteins were eluted from protein A beads and digested with endo H (+) or mock digested (–) at 37° C. before electrophoresis and autoradiography. In FIG. 3(D), human fibroblasts were infected with HSV-1 (F) for 0, 2, 4, 6, or 8 hours, were then pulse labeled for 30 minutes as in (A), and the label was chased for 90 minutes. MHC class I molecules were immunoprecipitated with antibody W6/32 and samples were either treated (+) or not treated (–) with endo H. A molecular mass marker of 45 KDa is indicated on the right.

The results show that Class I molecules immunoprecipitated from infected or uninfected cells were digested with endoglycosidase H (endo H), which removes high-mannose but not fully processed oligosaccharides, as a measure of glycoprotein transit through the medial and trans Golgi compartments (Townsend et al, 1989. Supra). MHC class I α-chains from uninfected cells became resistant to endo H after a 90 minutes chase period, while class I proteins from cells infected with HSV-1 or HSV-2 remained sensitive to endo H (FIG. 3A). The inhibition of MHC class I transport and processing in HSV-infected cells was apparently a specific effect rather than a general one, since HSV-1 glycoprotein D (gD) and the transferrin receptor were efficiently processed to become endo H-resistant during the 90 minutes chase period (FIG. 3B,C). When cells were infected with HSV-1 and examined at various times after infection, alterations in the processing of MHC class I was first observed 2 hours after infection with HSV-1 and the effect was complete by 4 hours (FIG. 3D). As expected, mouse H-2K$^b$ class I molecules expressed in human fibroblasts infected with F-US5MHC also remained in an endo H sensitive form, yet H-2K$^b$ and several other mouse MHC class I proteins expressed in HSV-infected mouse fibroblasts and other mouse cells became endo H resistant (data not shown). These results demonstrate that MHC class I complexes are retained in the endoplasmic reticulum/cis Golgi of human fibroblasts, but not mouse cells, soon after infection with either HSV-1 or HSV-2.

It is well established that processing of N-linked linked oligosaccharides occurs in the Golgi apparatus as glycoproteins are transported from the endoplasmic reticulum (ER) (site of synthesis and initial glycosylation) to the Golgi then to the cell surface. When glycoproteins do not become processed they do not reach the cell surface. Therefore, lack of processing indicated by endo H sensitivity (endo H recognizes immature, high mannose N-linked oligosaccharides but not mature complex N-linked oligosaccharides) is indicative of lack of transport to the cell surface (for review see: Kornfeld, R., and Kornfeld, S., *Assembly of asparagine-linked oligosaccharides*, Ann. Rev. Biochem. 54:631–664. (1985)).

Evidence that MHC I in HSV-infected cells is unstable

MHC class I polypeptides produced in RMA-S and T2 cells, lacking the putative peptide transporter proteins, were found to be misfolded and unstable (Townsend et al, 1989, Supra; Townsend, A., Elliott, T., Cerundolo, V., Foster, L., Barber, B., and Tse, A, *Assembly of MHC class I molecules analyzed in vitro*, Cell 62:285–295 (1990)). In order to examine the stability and folding of class I molecules in HSV-infected human fibroblasts, we carried out pulse-chase experiments in which we detected the MHC class I products with two antibodies, one which recognizes only properly folded MHC class I proteins, and another which recognizes both properly folded and misfolded ones.

Figure 4A:
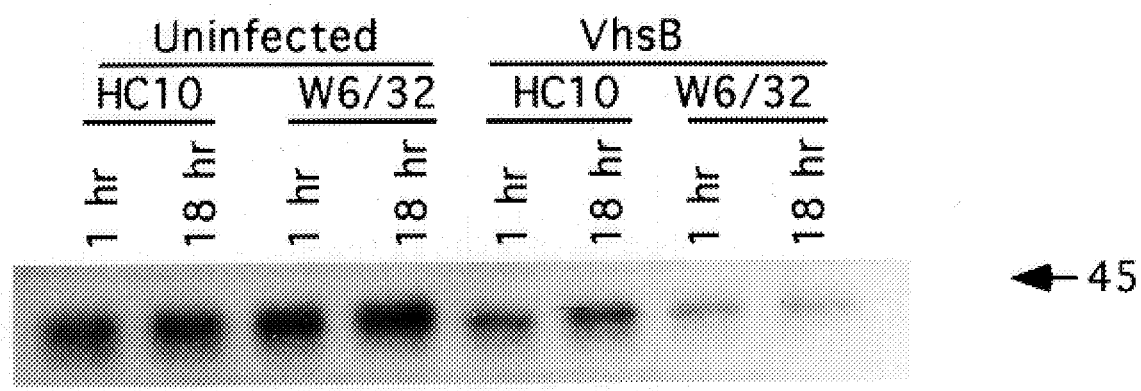
FIGS. 4(A) and 4(B) show electrophoretic 4(A) and quantitative 4(B) results of pulse chase experiments in which MHC class I products of uninfected cells and cells infected with an HSV-1 mutant lacking the virion host shut-off gene were detected with two antibodies, W6/32, which recognizes only properly folded MHC class I proteins, and HC10, which recognizes both properly folded and misfolded ones.
Figure 4B:
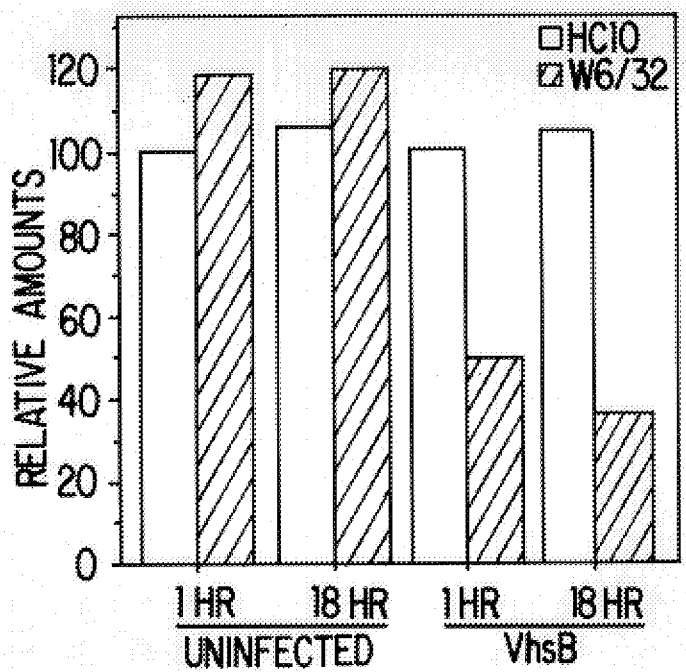

More specifically, in these experiments human fibroblasts were left uninfected or infected for 4 hours with HSV-1 VhsB, a mutant lacking the virion host shutoff gene, then the cells were radiolabeled for 1 hour with $^{35}$S-methionine and $^{35}$S-cysteine and the label was chased for 30 minutes. Cell extracts were mixed with antibodies immediately (1 hr) or were incubated for 18 hours on ice before being mixed with antibodies. MHC class I proteins were immunoprecipitated using monoclonal antibody W6/32, which recognizes only properly folded class I heavy/light chain complexes (Parham et al, 1979, Supra) or HC10 which, under the conditions used, recognizes misfolded as well as folded MHC class I α-chains (Stam et al, 1986, Supra), by first heating the cell extracts for 1 hour at 70° C. to denature the protein molecules. After immunoprecipitation, samples were subjected to electrophoresis on 14% polyacrylamide gels, as shown in FIG. 4(A); a molecular weight marker of 45 KD is shown at the right of the gel. A densitometric quantitation of protein bands corresponding to the class I α-chains was also performed, as shown in FIG. 4(B). The densitometric values obtained with uninfected and HSV-infected cell extracts incubated for 1 hours and precipitated with HC10 were set at 100.

As is apparent from FIG. 4, There was a modest inhibition of MHC class I α-chain synthesis in HSV-infected cells, even though an HSV-1 mutant unable to express the virion host shut-off function, vhs, was used (Smibert and Smiley, 1990, Supra); perhaps this was because of competition between cellular and viral transcription and translation factors. Densitometric quantitation of the protein bands immunoprecipitated by HC10 showed that there was no appreciable proteolytic degradation of the α-chain in either infected or uninfected cells during the 18 hours incubation at 4° C. However, only a fraction of the class I α-chains present in extracts from HSV-infected cells were recognized by W6/32. In the example shown, approximately 42% of the class I molecules precipitated by HC10 (total number of molecules) were recognized by W6/32 after 1 hours and about 30% of these molecules dissociated during 18 hours at 4° C. (FIG. 4). In contrast, class I molecules from uninfected cells were efficiently recognized by W6/32 and were stable, as less than 5% of the molecules dissociated during the 18 hours incubation. Therefore, it appears that MHC class I complexes formed in HSV-infected cells were misfolded and considerably less stable than those formed in uninfected cells.

In these experiments, β2-microglobulin levels were not dramatically altered by HSV infection (data not shown), and furthermore, this β2-microglobulin was available for binding to class I heavy chains because 45% of the heavy chain could be recognized by monoclonal W6/32, which recognizes only class I complexes containing β2-microglobulin.

It is known that folding of MHC class I proteins in the ER is dependent upon trimerization of MHC class I heavy or alpha chain, β2-microglobulin, and small peptides derived from cellular or viral proteins (reviewed in Yewdell and Bennick (1990), Supra). Townsend et al. (1990, Supra) and numerous others have shown that MHC class I molecules fail to assemble, fold improperly and are not transported to the cell surface in mutant cells if peptides are not available in the ER. Later studies indicated that this was because these mutant cells lack TAP proteins which "pump" peptides into the ER. In these mutant cells, e.g. RMA-S or 0.174, MHC class I proteins remain sensitive to endo H and are misfolded. Moreover, the observed misfolding and instability of the MHC class I complexes in HSV-infected fibroblasts is similar to that observed in TAP transporter-negative cell lines, and indicates that peptides are not associated with these MHC class I complexes in HSV-infected cells.

It has been found here that MHC class I proteins synthesized in HSV-infected cells have the same attributes, e.g., the class I proteins remain endo H sensitive and are misfolded, as indicated by their lack of recognition by a conformationally sensitive monoclonal antibody. Since their lack or processing means that the class I proteins do not reach the cell surface in HSV-infected cells, one predicts that the class I proteins would be defective in presenting viral antigens to T lymphocytes.

Evidence that the HSV-1 immediate-early gene product ICP47 is required for ER retention of MHC I HSV expresses three classes of gene products: immediate early (IE), early (E), and late (L), where IE proteins are required for the synthesis of E and L proteins (Honess, R. W. and Roizman, B., *Regulation of herpesvirus macromolecular synthesis. I. Cascade regulation of the synthesis of three groups of viral proteins*, J. Virol. 14:8–19 (1974)). However, a group of viral gene products including the vhs protein (McLaughlin, J., Addison, C., Craigie, M. C., and Rixon, F. J., *Noninfectious L-particles supply functions which can facilitate infection by HSV-1*, Virology 190:682–688 (1992)) and the VP16 transactivator of IE proteins (Batterson, W., and B. Roizman., *Characterization of the herpes simplex virion-associated factor responsible for the induction of α genes*, J. Virol. 46:371–377 (1983)) are incorporated into the virus particle and delivered into host cells upon virus entry. Since MHC class I proteins were retained in the ER within 2 hours following HSV-1 infection (FIG. 2), it appeared that either a virion structural protein or an immediate-early gene product was be responsible for the retention of those proteins.

To determine whether a virion structural protein was involved in this effect, stocks of HSV-2 were subjected to UW-inactivation so that the virus particles retained vhs activity but were transcriptionally silent. Human fibroblasts were left uninfected, infected with HSV-2 (333), or with HSV-2 (333-vhs⁻), a mutant derived from 333 which does not express the vhs function, using 10 plaque forming units/ml (PFU/ml). Other monolayers of fibroblasts were treated with gradient purified, UV-inactivated virus particles derived from HSV-2 strain 333 or 333-vhs⁻ at levels corresponding to 200 PFU/cell, and were incubated for 2 hours at 37° C. The cells were labeled using the pulse-chase protocol described for the experiments shown in FIG. 3, except that the pulse was for 20 min; then MHC class I proteins were immunoprecipitated using antibody W6/32, and class I proteins digested (+) or not digested (-) with endo H, as also described for the experiments shown in FIG. 3. The proteins were then subjected to electrophoresis on 14% polyacrylamide gels and exposed to X-ray film.

Figure 5A:
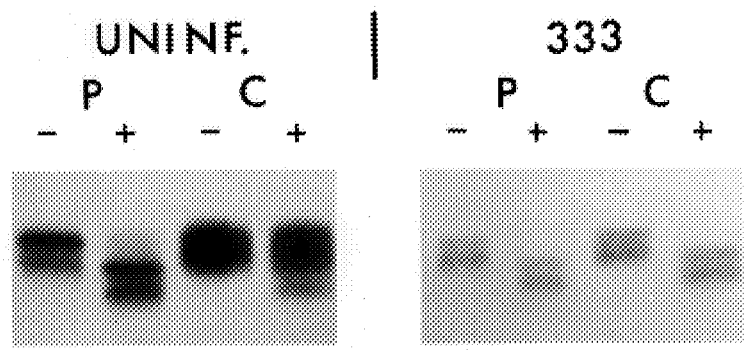
FIGS. 5(A), 5(B), and 5(C) show the autoradiograms obtained after electrophoresis of immunoprecipitated, pulsed and chased MHC class I α chain proteins, both with and without prior endoglycosidase H digestion, from cells that were infected with either HSV-2 strain 333, 5A, or a mutant lacking the virion-host shut-off function, 5B, or were alternatively infected with those same viruses after they were transcriptionally inactivated by irradiation with ultraviolet light, 5C.
Figure 5B:
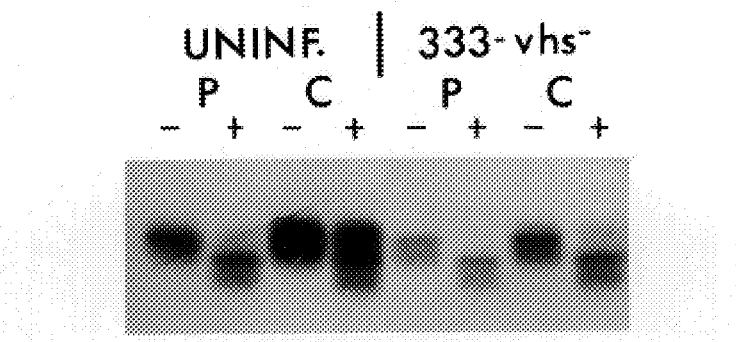
Figure 5C:
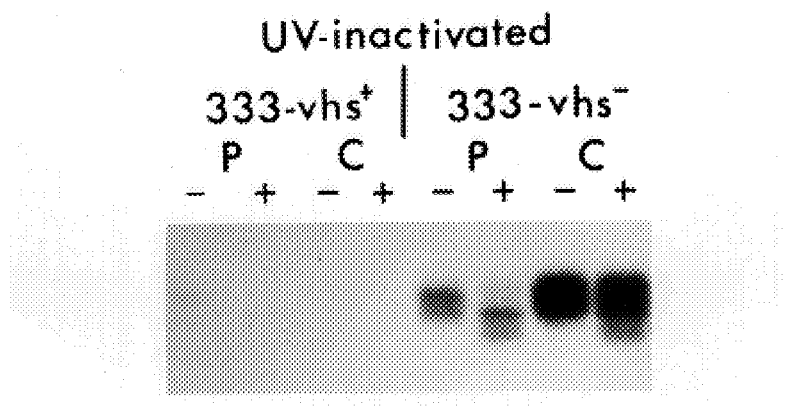

The results are shown in FIG. 5. In cells treated with relatively large quantities of UV-inactivated HSV-2 particles lacking the vhs protein (333vhs⁻), MHC class I proteins were processed in an identical fashion to that in uninfected cells; processing to endo H resistant forms after the chase period was not significantly inhibited. UV-inactivated virus particles derived from a HSV-2 strain which retained a wild type vhs gene (333-vhs+) produced a marked decrease in the expression of class I proteins under these conditions, demonstrating that the virus particles retained vhs activity after UV-inactivation which had shut off host transcription.

Since placing relatively high concentrations of structural proteins in the presence of cells was inadequate to inhibit the processing of MHC class I proteins to their endo H resistant forms, it appears that HSV-2 structural proteins and the vhs protein, which are part of the virus particle, are not sufficient to cause ER retention of MHC class I proteins, and that transcription of HSV genes is required.

In order to determine whether HSV IE proteins were capable of inhibiting processing of MHC class I proteins, a panel of HSV-1 mutants unable to express the 6 IE proteins was analyzed. Human fibroblasts were left uninfected (UN) or were infected with wild-type HSV 1(KOS), an HSV-1 lacking the virion host shutoff gene (KOS-vhs⁻); HSV-1 mutant dl120, which is unable to express ICP4; HSV-1 mutant ICP6Δ, which is unable to express ICP6; HSV-1 mutant R325-βTK+, which is unable to express ICP22; HSV-1 mutant 5dl1.2, which is unable to express ICP27; or HSV-1 mutant N38, which is unable to express ICP47. Cells were infected for 3 hr, were labeled with $^{35}$S-methionine and $^{35}$S-cysteine for 20 min, and were then immediately lysed (P) or the label was chased for 90 minutes (C) before lysis. MHC class I α-chains were immunoprecipitated using monoclonal antibody HC10 and the proteins either were treated with endo H (+) or were not treated (-) before electrophoresis and autoradiography.

Figure 6A:
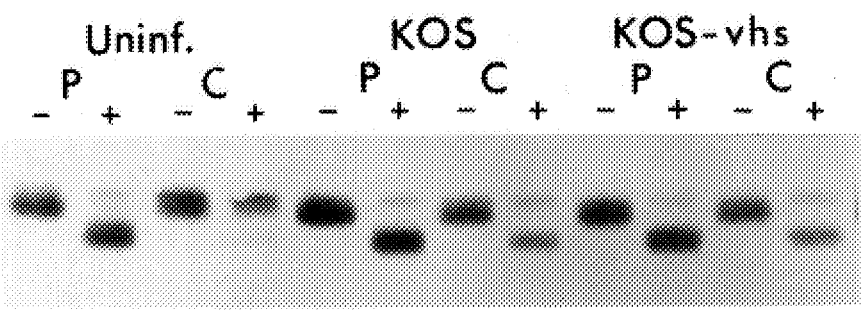
FIGS. 6(A), 6(B), and 6(C) show the autoradiograms obtained after electrophoresis of immunoprecipitated, pulsed and chased MHC class I α chain proteins, both with and without endoglycosidase H digestion, from cells infected with wild-type (KOS) HSV-1, and with HSV-1 mutants each defective in their ability to express a single gene, either the virion host shut-off gene (vhs−), 6A, or one of the genes for the immediate early proteins ICP4, ICP6 or, ICP0, 6B, ICP22, ICP27, and ICP47, 6C.
Figure 6B:
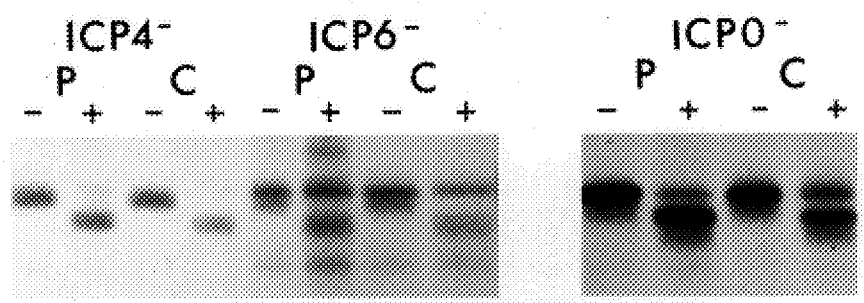
Figure 6C:
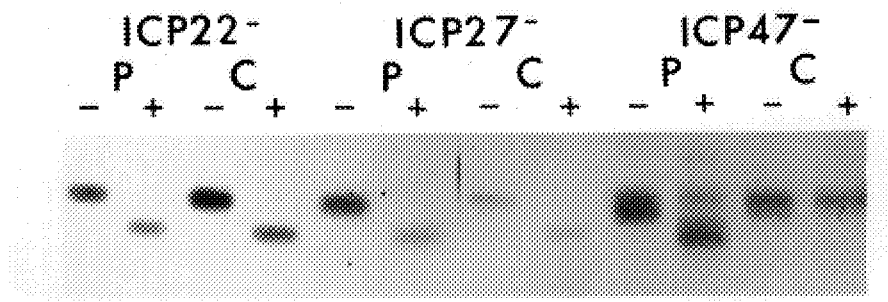

The results of these experiments are shown in FIG. 6. In cells infected with HSV-1 d120, a mutant unable to express IE protein ICP4, class I proteins remained endo H sensitive. Since ICP4 is strictly required for expression of both E and L proteins (Dixon, R. A. F., and Schaeffer, P. A., *Finestructure mapping and functional analysis of temperature-sensitive mutants in the gene encoding the herpes simplex virus type 1 immediate early protein VP175*, J. Virol. 36:189–203 (1980); Watson, R. J. and Clements, J. B., *A herpes simplex virus type 1 function continuously required for early and late virus RNA synthesis*, Nature 285:329–330 (1980)), this shows that expression of only the HSV-1 IE proteins is sufficient to inhibit class I processing and transport. Analysis of MHC class I proteins produced by mutants unable to produce IE proteins ICP6, ICP22, ICP27 and ICP0 (FIG. 6) shows that these mutants were still able to inhibit class I processing, as the proteins remained endo H sensitive. This indicates that these IE proteins are not essential to the inhibition of MHC class I protein processing.

In contrast, mutant N38, which is unable to express ICP47 (Nishiyama et al. (1993), Supra), did not block class I processing; the chased samples showed little or no endo H sensitivity, indicating that processing was completed or nearly completed by that time. We note that mutant N38 lacks coding sequences for the US9, US10, and US11 genes in addition to the lack of ICP47 coding sequences; however, The US9, US10 and US11 genes, which are early and late genes, were not be expressed in cells infected with mutant d120, which lacks the ICP4 gene function that is required for expression of early and late genes, and cells infected with this mutant still caused inhibition of MHC Class I processing (see above). Thus, it is unlikely that any of these genes are involved in this effect. In contrast, these results indicate that IE protein ICP47 is involved in inhibition of MHC class I protein processing and transport to the cell surface.

A second HSV-1 mutant, R3631, which lacks the ICP47 and US11 genes (Mavromara-Nazos, (1986), Supra), also failed to inhibit class I processing (not shown). ICP47 is an IE gene which does not require ICP4 for its expression, and it has no known effect on virus replication. Expression of the other IE genes, as well as E and L proteins, in cells infected with this mutant was normal (data not shown). This indicates that ICP47 is required for the observed inhibition of class I processing and transport, and that no other IE proteins are necessary.

Since MHC class I molecules must be transported to the cell surface so that cells can be recognized by CD8+ T lymphocytes, the observed inhibition of class I processing and transport caused by ICP47 would be expected to cause cells containing ICP47 to be resistant to these cytotoxic T lymphocytes.

As a final and conclusive proof that the gene for ICP47 alone is sufficient to produce the inhibition of MHC class I protein processing and transport, and that it is also sufficient to produce the inhibition of CTL lysis that is observed in HSV infections, the ICP47 gene has been cloned into an adenovirus vector. Studies on this vector have demonstrated that a vector carrying the ICP47 gene is able to produce the ICP47 protein, cause inhibition of MHC class I protein processing and transport, and inhibit cell lysis by cytotoxic T lymphocytes. Because these experiments are of great value in illustrating many of the uses for the ICP47 gene and its homologues that are part of this invention, they have been omitted here, and have instead been shown and described as part of Example 1 hereinbelow.

Improving the infective persistence of a mammalian virus by inserting genes for ICP47 or ICP47 homologues The use of viruses to serve as vectors for "gene therapy" is a promising technique, which may in the future be widely practiced. Simply stated, a gene encoding a protein having therapeutically desired effects is cloned into a viral expression vector, and that vector is then introduced to the target organism. The virus infects the cells, and then produces the protein sequence in vivo, where it has its desired therapeutic effect. (See, e.g., Zabner, J., Couture, L. A., Gregory, R. J., Graham, S. M., Smith, A. E., and Welsh, M. J., *Adenovirus-mediated gene transfer transiently corrects the chloride transport defect in nasal epithelia of patients with cystic fibrosis*, Cell 75:207–216 (1993)). However, one limitation of this use of viral vectors for gene therapy is that the infected cells get recognized and killed by the T lymphocytes, which eventually results in the loss of the virus and its beneficial therapeutic effect. Indeed, the concern that immune responses directed to viral proteins or to foreign gene therapy proteins might cause loss of gene therapy vectors is a major concern in the field of gene therapy (Id.).

The present invention offers a method by which the infective persistence of viral gene therapy vectors might be improved, thus enhancing the therapeutic value of those vectors. This method entails adding to the vector a sequence that encodes the ICP47 protein, the IE 12 protein of HSV-2, or another protein substantially homologous to ICP47. Once these sequences are added to the vector, the expression of those sequences should effectively inhibit CD8+ T lymphocyte recognition of infected cells, and should thereby enhance the longevity and virility of the beneficial virus.

One embodiment of this aspect of the invention is shown in Example 1 hereinbelow, wherein the ICP47 gene has been isolated and inserted into an adenovirus vector. This vector is thereafter able to inhibit the processing and transport of MHC class I proteins, and to thereby inhibit cell lysis by cytotoxic T lymphocytes that are directed against a virus with which the cells were coinfected. This demonstrates that such a vector or vector element could be used to protect the cells in which they reside from CTL-mediated cell lysis, whether the desired gene therapy gene was carried on that vector or on another vector with which the recipient was to be coinfected. Since it is the ICP47 gene product that causes the inhibition, these experiments suggest that delivering the ICP47 protein or a protein substantially homologous to it into the cells would have a similar effect. Such proteins could be produced using known molecular biology methodologies (See: Sambrook et al, 1989, Supra).

Of course, the foregoing should not be viewed as limited to gene therapy vectors, as this method could be used to improve persistence in any virus in which such persistence may be desired.

The present invention also includes the vector elements that might be used to carry out this method. It is possible to use only the protein coding regions for such purpose, or to use the entire genes, including introns and other elements. The 714bp NruI-XhoI fragment of pRHP6, including part of the first exon, the intron, and the entire coding sequences of ICP47, is one such element. Adenovirus vector AdICP47-1 is a gene therapy vector that includes this element.

Inserting genes for ICP47 or ICP47 homologues into somatic genes or secondary vectors to inhibit cell recognition As an alternative to adding the sequences encoding ICP47 or a homologous protein to the DNA of a virus, it is also possible to introduce such a gene into the somatic DNA of infected or uninfected cells, by methods that are well known in the art (Sambrook et al. 1989, Supra). Alternatively, it is also possible to introduce such a sequence into infected or uninfected cells by use of a secondary virus, i.e., one that is not the virus that is expected to produce the immune response. For example, it may be desirable to introduce such a secondary virus carrying an ICP47 coding sequence prior to the introduction of a viral gene therapy vector. This possibility is well illustrated by Example 1 hereinbelow; the gene for ICP47 is carried on an adenovirus vector, yet is demonstrably able to inhibit cell lysis by cytotoxic T lymphocytes specific for cytomegalovirus, with which the cells were co-infected. Thus, it is clear to one of ordinary skill in the art that one vector carrying the gene for ICP47 or a homologous protein could be used to infect a patient, and that a second vector, e.g., a virus carrying a gene to be introduced by gene therapy, could be used to infect that same individual; the first vector would inhibit recognition by CTL directed against either vector.

Additionally, it may be quite useful to introduce a sequence that codes for ICP47 or a homologous protein into the cells of individuals suffering from autoimmune diseases, either by introducing it into the somatic DNA or into a viral gene therapy vector, or alternatively, to introduce the protein ICP47 or its homologue into the patient's cells. By doing so, it should be possible to limit the display of MHC Class 1 complexes, and thereby limit autoimmune responses and symptoms of the disease. This approach should be useful in the treatment of a number of disorders believed to be in part mediated by cytotoxic T lymphocytes, such as tissue and organ transplant rejection, diabetes, multiple sclerosis and arthritis, whether or not they are wholly "autoimmune disorders" as that term is generally used. By reducing the recognition of cells of involved tissues by cytotoxic T lymphocytes, the symptoms of the disorder should be reduced. It should also be of value to use such a therapy with patients at high risk for developing such disorders, even if the damaging symptoms have not yet appeared. Furthermore, this approach should also be of value in the treatment of ocular herpesvirus infections, where significant tissue damage occurs as a result of cytotoxic T lymphocyte activity; this approach should lead to a reduction in recognition of cells by T lymphocytes, and thereby reduce tissue damage. Similarly, it should be possible to use this method to treat transplant recipients in order to limit CD8+ T lymphocyte-mediated tissue rejection.

In some of the foregoing examples, it may only be necessary to introduce the genetic or protein elements into certain cells or tissues. For example, in the case of diabetes, introducing them into only the pancreas should be sufficient, and in the case of tissue or organ transplants, to only introduce them into the tissues or organ being transplanted. However, it may be more therapeutically effective and more simple to treat all of the patients cells.

Each of the above objectives should be equally attainable by adding to the cells the ICP47 protein itself, or a homologous protein, which could be easily produced by known recombinant DNA methodologies. (Sambrook et al., 1989, Supra).

Treating persistent herpesvirus infections by use of antisense strands targeted to a ICP47 homologous mRNA or gene There is now a considerable art regarding the use of so-called "anti-sense" polynucleotide sequences or analogs to prevent the expression of proteins in vivo (for review see: Neckers, L. and Whitesell, L., *Antisense Technology: biological utility and practical considerations*, Am. J. Physiol. 265 (Lung Cell. Mol. Physiol. 9:) L1–L12 (1993)). The basic theory is that if you add to a cell a large number of strands of a nucleotide sequence that is complementary to the messenger RNA that is transcribed to produce a particularly protein, these "anti-sense" strands will hybridize to the mRNA and limit or prevent its transcription. This method could be used here to limit or prevent the expression of ICP47 and homologous proteins by herpesviruses; as a result, suppression of immune recognition by CD8+ T lymphocytes would be reduced, and the organism's immune system could more rapidly and effectively kill the infected cells. It is possible that this will even make it possible to eliminate the recurring symptoms of herpesvirus infection; e.g., in HSV-1 infections, it might be possible to prevent recurring "fever blisters".

Treating herpesvirus infections with antibodies against an ICP47 homologous protein Persistent herpesvirus infections may also be advantageously treated by introducing monoclonal or polyclonal antibodies to the ICP47-homologous protein that the given virus produces; this will limit or prevent the suppression of MHC Type I complex expression, and thus allow for more effective immune clearing. Methods for intracellular description of antibodies have been described (See. e.g. Carlson, J. R., *A new use for intracellular antibody expression: inactivation of human immunodeficiency virus type 1*, Proc. Natl. Acad. Sci. U.S.A. 90:7427–7428 (1993)).

Treating herpesvirus infections with drugs which interrupt or inhibit ICP47

ICP47 appears to block availability of cellular or viral peptides which would normally be presented on MHC class I molecules, causing the MHC class I molecules to become misfolded and preventing their transport to the cell surface. Whatever the mechanism of ICP47 action, however, it is reasonable to conclude that ICP47 achieves its effect by interaction with one or more intracellular protein or other molecule. Furthermore, it is clear that inhibition of MHC class I protein display depends on synthesis of ICP47, and it seems reasonable to conclude that its effectiveness is to at least some extent dose-dependent.

With these things in mind, it seems clear that by blocking the synthesis of ICP47 or its homologues, or by interfering with the interaction between ICP47 or its homologues and cellular molecules using drugs specifically developed for this purpose, one would expect that cells infected with herpesvirus would be more readily recognized by antiherpesvirus CD8+ T lymphocytes, leading to better recognition of herpesviruses by the immune system, with the beneficial results of reduced infection, decreased latency, and reduced symptoms.

The invention as described herein includes a method to screen for such drugs, as well as the drugs so identified. Quite simply, one need only create a system that produces ICP47 or a homologue of it, add amounts of candidate compounds to that system, and determine whether synthesis of ICP47 or the homologue is inhibited, whether inhibition of the processing of MHC class I proteins decreases, or whether cytotoxic T lymphocyte lysis of cells increases when compared to that same system in the absence of the added compound. Candidate compounds could include a wide spectrum of small molecules from which so-called "ethical pharmaceuticals" are often identified, and could also include a wide variety of other compounds, including large and small synthetic compounds, as well as many naturally-occurring or man-made biomolecules, including polynucleotides and polypeptides.

One could easily use one or more of the methods described herein to accomplish this. For example, one might establish a model system that produces ICP47, either because it carries the coding gene in its genome, on a vector, or in a virus with which it has become infected. One could then test for decreased ICP47 synthesis by using the ICP47 antibody detection method used to produce the results shown in FIG. 7; test for an increase in endo H resistance of the MHC class I complexes by using a pulse-chase protocol as was used to produce the results shown in FIG. 6; and/or test for increased CTL lysis using the assay method used to produce the results shown in FIG. 2 or FIG. 8.

EXAMPLE 1

Construction and characterization of a recombinant adenovirus vector carrying the coding sequence for HSV-1 ICP47

Figure 7A:
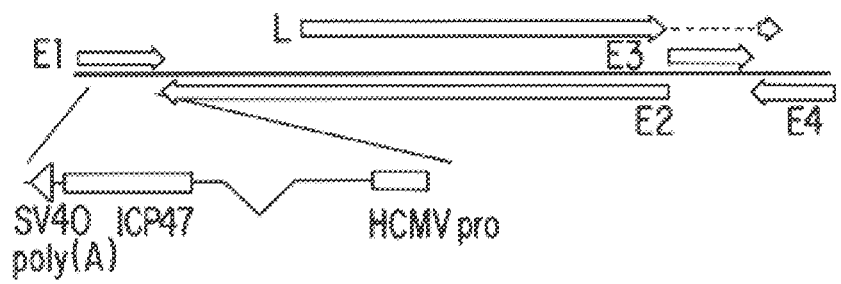
FIG. 7(A) is a diagram of the recombinant adenovirus vector designated AdICP47-1.

To determine whether other HSV gene products were required for the inhibition of antigen processing and whether ICP47 was sufficient for this effect, we constructed a recombinant adenovirus vector, AdICP47-1. As shown in FIG. 7(A), the HSV-1 ICP47 gene was placed under the control of the HCMV immediate early promoter and was inserted into the E1 region of adenovirus type 5 to produce AdICP47-1. AdICP47-1 is replication defective because it lacks Adenovirus E1 sequences as well as E3 sequences.

Expression of ICP47 proteins

Figure 7B:
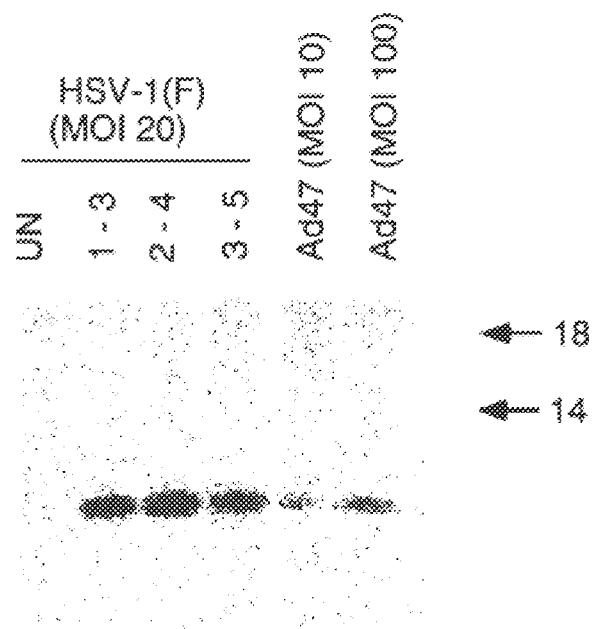
FIG. 7(B) shows the electrophoresis pattern obtained when an ICP47-specific antibody was used to precipitate radiolabeled proteins produced by cells infected with wild-type HSV-1 or with adenovirus vector AdICP47-1.

The expression of ICP47 was examined by infecting human fibroblasts with HSV-1(F) using 10 PFU/cell or AdICP47-1 (Ad47) using either 10 or 100 PFU/cell, or leaving fibroblasts uninfected (UN). Cells were labeled for 2 hr. HSV-infected cells were radiolabeled from 1 to 3, 2 to 4, or 3 to 5 hours after infection, and AdICP47-1-infected cells were radiolabeled from 36 to 38 hours after infection using $^{35}$S-methionine and $^{35}$S-cysteine (50 uCi/ml of each). ICP47 was immunoprecipitated using an ICP47-specific antipeptide serum and subjected to electrophoresis using 16% polyacrylamide gels. As shown in FIG. 7(B), proteins of the same molecular weight as ICP47 were produced by AdICP47-1 (lanes are marked "Ad47" in the figure legend), and these reacted with ICP47-specific antibodies. It therefore appears that the adenovirus vector AdICP47-1 is able to produce the ICP47 protein in vivo.

MHC class I transport and processing is inhibited

Figure 7C:
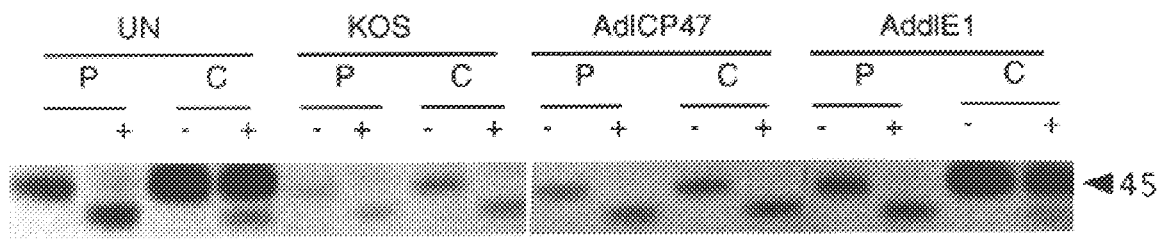
FIG. 7(C) shows the autoradiograms obtained after electrophoresis of immunoprecipitated, pulsed and chased MHC class I α chain proteins, both with and without endoglycosidase H digestion, from human fibroblast cells infected with wild-type HSV-1(KOS), AdICP47-1, or AddlE1 (which does not express ICP47)

In order to determine whether the ICP47 proteins produced upon infection of cells with adenovirus vector AdICP47–1 were able to inhibit intracellular MHC class I protein processing, human fibroblasts were left uninfected or were infected with HSV-1(KOS), AdICP47–1, or AddlE1 (which lacks E1 and E3 sequences but does not express ICP47). Four hours after infection with HSV 1 or 36 hours after infection with an adenovirus, the cells were radiolabeled with $^{35}$S-methionine and $^{35}$S-cysteine for 30 minutes and immediately lysed (P) or the label chased for 90 minutes (C) before lysis. MHC class I α-chains were immunoprecipitated using monoclonal antibody HC10 and treated with endo H (+) or not treated (-) before electrophoresis and autoradiography. The results are shown in FIG. 7(C); a molecular weight marker of 45 KDa is shown at the right.

These results show that MHC class I proteins produced in human fibroblasts infected with AdICP47-1 remained sensitive to Endo H, as with HSV-1-infected human fibroblasts. Class I molecules from cells infected with control adenovirus AddlE1, lacking E1 and E3 sequences, became largely endo H resistant. These results show that the ICP47 protein produced by the recombinant adenovirus vector AdICP47-1 is able to inhibit MHC class I protein processing in vivo.

Similar results were obtained with another adenovirus vector, AdICP47-3, where ICP47 coding sequences were placed under control of the SV40 early promoter and inserted into the E3 region so that the E1 sequences were intact and the adenovirus vector was capable of replicating in human cells (data not shown). Therefore, other HSV gene products are not required for this effect and expression of HSV ICP47 is sufficient to prevent MHC I transport and processing.

Lysis by specific cytotoxic T lymphocytes is inhibited

In order to determine if ICP47 produced by an adenovirus vector could inhibit recognition by cytotoxic T lymphocytes, human MR fibroblasts were left uninfected (UN) or were infected with AdICP47-1 or AddlE1 for 36 hours, and were then infected with human cytomegalovirus (CMV) for 12 to 16 hours. An allogeneic fibroblast cell line, DG, was also infected with CMV. The fibroblasts were then loaded with the radiolabel $^{51}$Cr and mixed with various ratios (effector:target cell ratios or E:T ratios) of a human cytomegalovirus-specific cytotoxic T lymphocyte clone, MR-16E6. Release of $^{51}$Cr was determined after 5 hours, and percent specific lysis of the fibroblasts was calculated.

Figure 8:
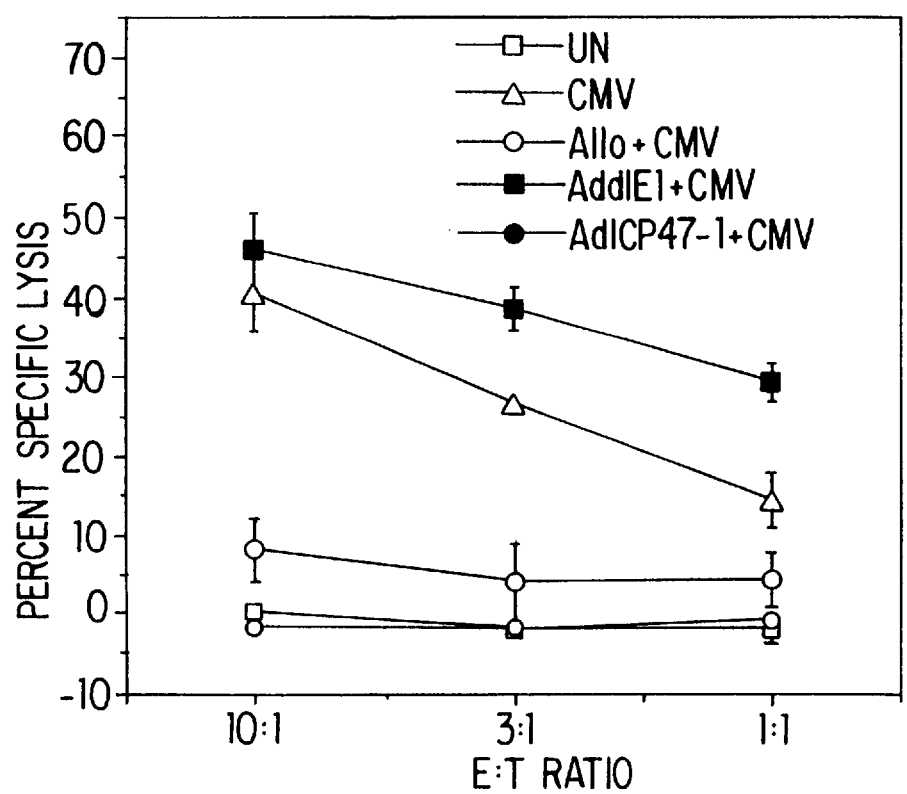
FIG. 8 shows the results of human cytomegalovirus-specific cytotoxic T lymphocyte lysis assays on human MR fibroblast cells that were uninfected, infected with human cytomegalovirus (CMV), or were infected with AdICP47-1 or AddlE1 followed by infection by CMV, and a similar assay on human allogeneic DG fibroblast cells that were subsequently infected by CMV.

The results are shown in FIG. 8. Uninfected fibroblasts (UN) were not lysed by the HCMV specific clone (I.E., no $^{51}$Cr was released after mixing with the cytotoxic T lymphocytes) but 40% to 50% of the $^{51}$Cr was released from HCMV-infected fibroblasts (CMV) indicating that there was specific lysis of these cells. Lysis of allogeneic DG fibroblasts (Allo+CMV), which do not share the same MHC class I molecules as the cytotoxic T lymphocytes, did not occur, indicating that the cytotoxic T lymphocyte clone lysed only target cells which shared the same MHC class I molecules. Prior infection of the fibroblasts with AdICP47-1 caused the lysis of fibroblasts subsequently infected with HCMV (AdICP47+CMV) to be reduced to background levels. By contrast, prior infection of cells with AddlE1 had no effect on the lysis of cells infected with HCMV (AdICP47+CMV). Therefore, expression of ICP47 blocked lysis of the cells by a cytotoxic T lymphocyte clone.

It is understood that the examples and embodiments described herein are for illustrative purposes only, and that various modifications or changes in light thereof will be suggested to persons skilled in the art; these are to be included within the spirit and purview of this application and scope of the appended claims.

We claim:

1. A method of inhibiting recognition of a cell by cytotoxic T lymphocytes, comprising introducing into said cell an isolated protein selected from the group consisting of ICP47 of HSV type 1 and IE12 of HSV type 2.

2. The method of claim 1 wherein said protein is introduced to said cell by infecting the cell with a viral vector element encoding said protein.

* * * * *

UNITED STATES PATENT AND TRADEMARK OFFICE
CERTIFICATE OF CORRECTION

PATENT NO. : 5,858,376                                      Page 1 of 3
DATED      : 12 January 1999
INVENTOR(S) : David C. JOHNSON et al.

It is certified that error appears in the above-indentified patent and that said Letters Patent is hereby corrected as shown below:

| Column | Line | |
|---|---|---|
| 1 | 41 | Before "which" insert --,--. |
| 2 | 28 | Change "β²" to --$β_2$--. |
| 2 | 59 | Change "Ela" to --E1a--. |
| 3 | 5 | Change "histocomoatibility" to --histocompatibility--. |
| 3 | 12 | Change "histocomoatibility" to --histocompatibility--. |
| 4 | 13 | Change "(1992)." to --(1992)).--. |
| 8 | 66 | Change "FUS5β" TO --F-US5β--. |
| 12 | 56 | Change "*Heroes*" to --*Herpes*--. |
| 13 | 15 | Change "5dl.1.2," to --5dl1.2,--. |
| 13 | 62 | Change "pVc β2" to --pVcβ2--. |

UNITED STATES PATENT AND TRADEMARK OFFICE
CERTIFICATE OF CORRECTION

PATENT NO. : 5,858,376
DATED : 12 January 1999
INVENTOR(S) : David C. JOHNSON et al.

It is certified that error appears in the above-indentified patent and that said Letters Patent is hereby corrected as shown below:

| Column | Line | |
|---|---|---|
| 15 | 9-10 | Change "A simple technique for the rescue of early Region I mutations int infectious human adenovirus type 5." to --*A simple technique for the rescue of early Region I mutations int infectious human adenovirus type 5.*--. |
| 15 | 62 | Change "human: $\beta_2$m" to --human $\beta_2$m--.. |
| 16 | 10 | Change "*heroes*" to --*herpes*--. |
| 16 | 27 | After "100" delete ",". |
| 16 | 40 | Change "1-1.5" to --1-1.5 hr.--. |
| 16 | 49 | Change "40%" to --4%-- (two occurrences). |
| 17 | 65 | Change "CD8+" to --$CD8^+$--. |

UNITED STATES PATENT AND TRADEMARK OFFICE
CERTIFICATE OF CORRECTION

PATENT NO. : 5,858,376

DATED : 12 January 1999

INVENTOR(S) : David C. JOHNSON et al.

It is certified that error appears in the above-indentified patent and that said Letters Patent is hereby corrected as shown below:

| Column | Line | |
|---|---|---|
| 18 | 3 | Change "μ2" to --$\beta_2$--. |
| 18 | 67 | Change "βchain" --α chain--. |
| 19 | 42 | After "N-linked" delete "linked". |
| 21 | 36 | Change "UW-inactivation" to --UV-inactivation--. |
| 25 | 39 | Change "description" to --introduction--. |
| 26 | 63 | Change "HSV 1" to --HSV-1--. |

Signed and Sealed this

Twenty-third Day of November, 1999

Attest:

Q. TODD DICKINSON

Attesting Officer     Acting Commissioner of Patents and Trademarks